US012035865B2

(12) United States Patent
Boyer et al.

(10) Patent No.: US 12,035,865 B2
(45) Date of Patent: Jul. 16, 2024

(54) HIGH SPEED REUSABLE BEVERAGE CONTAINER WASHING SYSTEM WITH CONCENTRIC HOUSING MEMBERS

(71) Applicant: Midea Group Co., Ltd., Foshan (CN)

(72) Inventors: Joel Boyer, Louisville, KY (US); Robert M. Digman, Goshen, KY (US)

(73) Assignee: MIDEA GROUP CO., LTD., Guangdong (CN)

( * ) Notice: Subject to any disclaimer, the term of this patent is extended or adjusted under 35 U.S.C. 154(b) by 106 days.

(21) Appl. No.: 17/490,884

(22) Filed: Sep. 30, 2021

(65) Prior Publication Data
US 2023/0100978 A1    Mar. 30, 2023

(51) Int. Cl.
| | |
|---|---|
| *A47L 15/42* | (2006.01) |
| *A47L 15/00* | (2006.01) |
| *A47L 15/46* | (2006.01) |
| *A47L 15/48* | (2006.01) |
| *A61L 2/10* | (2006.01) |

(52) U.S. Cl.
CPC ....... *A47L 15/0065* (2013.01); *A47L 15/0021* (2013.01); *A47L 15/0076* (2013.01); *A47L 15/4242* (2013.01); *A47L 15/4257* (2013.01); *A47L 15/46* (2013.01); *A47L 15/486* (2013.01); *A61L 2/10* (2013.01); *A47L 2401/26* (2013.01); *A47L 2501/22* (2013.01); *A61L 2202/11* (2013.01); *A61L 2202/14* (2013.01)

(58) Field of Classification Search
CPC .............. A47L 15/0065; A47L 15/0076; A47L 15/0073; A47L 15/486; A47L 15/46; A47L 15/4242; A47L 15/0021; A47L 15/4257; A47L 2401/26; A47L 2501/22
See application file for complete search history.

(56) References Cited

U.S. PATENT DOCUMENTS

| 1,502,131 A | | 2/1922 | Vaudreuil |
|---|---|---|---|
| 1,680,962 A | * | 8/1928 | Voshardt ............. A47L 15/0081 220/252 |

(Continued)

FOREIGN PATENT DOCUMENTS

| CN | 2834716 Y | 11/2006 |
|---|---|---|
| CN | 201529653 U | 7/2010 |

(Continued)

OTHER PUBLICATIONS

Related Applications Transmittal dated Jul. 7, 2022.
(Continued)

*Primary Examiner* — Joseph L. Perrin
*Assistant Examiner* — Irina Graf
(74) *Attorney, Agent, or Firm* — Gray Ice Higdon

(57) ABSTRACT

A beverage container washing system may be used for rapid washing and/or sanitizing of beverage containers, e.g., for use in a retail environment to wash and/or sanitize customer-provided beverage containers prior to filling the beverage containers with purchased beverages, among other applications. The beverage container washing system may include multiple concentric housing members supported on a base, with each having one or more openings that may be selectively aligned through driven movement of at least one of the concentric housing members to provide access to a wash chamber.

16 Claims, 21 Drawing Sheets

(56) References Cited

U.S. PATENT DOCUMENTS

| | | | |
|---|---|---|---|
| 1,859,302 A * | 5/1932 | Lederman | A47L 15/4257 134/179 |
| 1,876,895 A | 9/1932 | James | |
| 2,263,807 A | 11/1941 | Hanson | |
| 2,634,736 A | 4/1953 | Bewen | |
| 2,764,171 A | 9/1956 | Nolte | |
| 2,970,700 A | 2/1961 | Lacy et al. | |
| 3,060,946 A | 10/1962 | David | |
| 3,204,273 A | 9/1965 | Gallo | |
| 3,312,230 A | 4/1967 | Thring | |
| 3,620,232 A | 11/1971 | Angelo | |
| 3,969,137 A | 7/1976 | Jenkins | |
| 4,444,213 A * | 4/1984 | Taylor | A47L 15/32 134/56 D |
| 4,561,904 A | 12/1985 | Eberhardt, Jr. | |
| 4,634,052 A | 1/1987 | Grizzle et al. | |
| 4,681,260 A | 7/1987 | Cochran | |
| 4,768,534 A | 9/1988 | Anderson | |
| 5,209,246 A | 5/1993 | Tromblee | |
| 5,249,590 A | 10/1993 | Jacobus | |
| 5,315,729 A | 5/1994 | Yang | |
| 5,343,886 A | 9/1994 | Beswick | |
| 5,522,410 A | 6/1996 | Meilleur | |
| 5,531,383 A | 7/1996 | Pacht et al. | |
| 5,640,981 A | 6/1997 | Niemela et al. | |
| 5,704,380 A | 1/1998 | Zelniker et al. | |
| 5,903,944 A | 5/1999 | Burrell | |
| 5,904,163 A | 5/1999 | Inoue et al. | |
| 6,086,222 A | 7/2000 | Juba et al. | |
| 6,110,424 A | 8/2000 | Maiden et al. | |
| 6,517,776 B1 | 2/2003 | Rodgers et al. | |
| 6,550,489 B1 * | 4/2003 | Yates | B08B 3/02 134/158 |
| 6,579,495 B1 | 6/2003 | Maiden | |
| 6,691,536 B2 | 2/2004 | Severns et al. | |
| 6,732,950 B2 | 5/2004 | Ingham, Jr. et al. | |
| 6,799,732 B2 | 10/2004 | Sirkin | |
| 6,926,017 B2 | 8/2005 | Halbmaier | |
| D516,757 S | 3/2006 | Hedstrom | |
| 7,236,099 B2 | 6/2007 | Schult | |
| 7,550,935 B2 | 6/2009 | Lys et al. | |
| 7,674,001 B1 | 3/2010 | Ferrin et al. | |
| 7,882,591 B2 | 2/2011 | Arnold | |
| 8,136,742 B2 | 3/2012 | Cordua | |
| 8,297,533 B2 | 10/2012 | Dunn et al. | |
| 8,303,728 B2 | 11/2012 | Peukert et al. | |
| 8,500,919 B1 | 8/2013 | Al-qaffas | |
| 8,810,423 B2 | 8/2014 | Kaczmarek et al. | |
| 8,905,014 B2 | 12/2014 | Shaffer | |
| 9,138,768 B2 | 9/2015 | Jahan et al. | |
| 9,146,032 B2 | 9/2015 | Maxwell | |
| 9,378,988 B2 | 6/2016 | Osada et al. | |
| 9,474,432 B2 | 10/2016 | Alexander | |
| 9,566,617 B2 | 2/2017 | Jensen et al. | |
| 9,596,972 B2 | 3/2017 | Sonoda | |
| 9,623,447 B2 | 4/2017 | Kataoka | |
| 9,707,306 B2 | 7/2017 | Farren | |
| 9,955,844 B2 | 5/2018 | Fletty et al. | |
| 10,047,922 B2 | 9/2018 | Chien | |
| 10,415,176 B2 | 9/2019 | Abramovich et al. | |
| 10,670,619 B2 | 6/2020 | Schulze et al. | |
| 10,893,790 B2 | 1/2021 | Ashworth et al. | |
| 10,921,059 B2 | 2/2021 | Newland, III et al. | |
| 2003/0150475 A1 | 8/2003 | Abrams et al. | |
| 2004/0250837 A1 | 12/2004 | Watson | |
| 2005/0072449 A1 * | 4/2005 | Alpert | A47L 15/46 134/25.1 |
| 2005/0199267 A1 | 9/2005 | Oakes | |
| 2005/0230638 A1 | 10/2005 | Ancona et al. | |
| 2006/0011263 A1 | 1/2006 | Till | |
| 2007/0034234 A1 | 2/2007 | Holzman | |
| 2007/0246071 A1 | 10/2007 | Streb | |
| 2008/0041419 A1 | 2/2008 | Gaus | |
| 2010/0132111 A1 * | 6/2010 | Na | A47L 15/14 4/654 |
| 2011/0056527 A1 | 3/2011 | Classen | |
| 2011/0203616 A1 | 8/2011 | Berner et al. | |
| 2012/0048300 A1 | 3/2012 | Thiyagarajan | |
| 2012/0141322 A1 | 6/2012 | Fogg | |
| 2012/0312337 A1 | 12/2012 | Boyer | |
| 2013/0198786 A1 | 8/2013 | Cook et al. | |
| 2014/0332041 A1 | 11/2014 | Feddema | |
| 2015/0047679 A1 | 2/2015 | Dreossi | |
| 2015/0182103 A1 | 7/2015 | Jung | |
| 2016/0345797 A1 | 12/2016 | Anim-Mensah | |
| 2018/0028044 A1 | 2/2018 | Anim-Mensah et al. | |
| 2018/0092505 A1 | 4/2018 | Simon | |
| 2018/0116483 A1 | 5/2018 | Glass | |
| 2018/0125325 A1 | 5/2018 | Buser | |
| 2018/0128137 A1 | 5/2018 | Case | |
| 2018/0168428 A1 | 6/2018 | Wilson | |
| 2018/0236398 A1 | 8/2018 | Heer et al. | |
| 2018/0318886 A1 | 11/2018 | Libbrecht et al. | |
| 2018/0338665 A1 | 11/2018 | Foehringer | |
| 2018/0354467 A1 | 12/2018 | Glickman et al. | |
| 2020/0216332 A1 | 7/2020 | Li | |
| 2020/0237179 A1 | 7/2020 | Haegermarck | |
| 2020/0253450 A1 | 8/2020 | Kafzan et al. | |
| 2020/0289685 A1 | 9/2020 | Li | |
| 2020/0337522 A1 | 10/2020 | Brewer et al. | |
| 2021/0161356 A1 | 6/2021 | Luu et al. | |
| 2021/0178434 A1 | 6/2021 | Van Pottelbergh et al. | |
| 2021/0308301 A1 | 10/2021 | Sperry | |
| 2022/0018531 A1 | 1/2022 | Mo et al. | |
| 2022/0079413 A1 | 3/2022 | Longo et al. | |
| 2022/0104681 A1 | 4/2022 | Beck | |
| 2022/0240750 A1 | 8/2022 | Held | |
| 2022/0338706 A1 | 10/2022 | Disch | |
| 2023/0095081 A1 | 3/2023 | Boyer et al. | |
| 2023/0097782 A1 | 3/2023 | Trice et al. | |
| 2023/0101333 A1 | 3/2023 | Boyer et al. | |
| 2023/0101384 A1 | 3/2023 | Longo et al. | |
| 2023/0102987 A1 | 3/2023 | Boyer et al. | |
| 2023/0101450 A1 | 4/2023 | Boyer et al. | |
| 2023/0112411 A1 | 4/2023 | Digman et al. | |
| 2023/0263363 A1 | 8/2023 | Boyer | |

FOREIGN PATENT DOCUMENTS

| | | |
|---|---|---|
| CN | 102324396 A | 1/2012 |
| CN | 203426095 U | 2/2014 |
| CN | 204363929 U | 6/2015 |
| CN | 205110293 U | 3/2016 |
| CN | 105534437 A | 5/2016 |
| CN | 108703731 A | 10/2018 |
| CN | 109876169 A | 6/2019 |
| CN | 209915722 U | 1/2020 |
| CN | 209967112 U | 1/2020 |
| CN | 212166190 U | 12/2020 |
| CN | 213191400 U | 5/2021 |
| CN | 213551016 U | 6/2021 |
| CN | 113500070 A | 10/2021 |
| CN | 113953276 A | 1/2022 |
| CN | 113953280 A | 1/2022 |
| CN | 113953281 A | 1/2022 |
| DE | 4229250 A1 | 3/1994 |
| DE | 4234598 A1 | 4/1994 |
| DE | 19618770 A1 | 11/1997 |
| DE | 102012109360 A1 | 5/2014 |
| DE | 102014222586 A1 | 5/2016 |
| DE | 102019106248 A1 | 10/2019 |
| DE | 102019214059 A1 | 3/2021 |
| EP | 1120121 A2 | 8/2001 |
| EP | 1183983 A2 | 3/2002 |
| EP | 2559369 A2 | 2/2013 |
| EP | 2703724 A1 | 3/2014 |
| EP | 3636333 A1 | 4/2020 |
| EP | 3788936 A1 | 3/2021 |
| EP | 3967207 A1 | 3/2022 |
| ES | 1265944 U | 4/2021 |
| FR | 1426408 A | 1/1966 |
| FR | 3068232 A1 | 1/2019 |

(56) References Cited

FOREIGN PATENT DOCUMENTS

| | | | |
|---|---|---|---|
| GB | 309878 | A | 4/1929 |
| IL | 108864 | A | 3/1999 |
| JP | 2001247108 | A | 9/2001 |
| KR | 20030017203 | A * | 3/2003 |
| KR | 101630417 | B1 | 6/2016 |
| KR | 20160065051 | A | 6/2016 |
| KR | 20180051462 | A | 5/2018 |
| KR | 101885722 | B1 | 9/2018 |
| KR | 101983721 | B1 | 5/2019 |
| KR | 101987953 | B1 | 6/2019 |
| KR | 102052837 | B1 | 12/2019 |
| WO | WO0244637 | A1 | 6/2002 |
| WO | 2005018407 | A2 | 3/2005 |
| WO | WO2005087276 | A2 | 9/2005 |
| WO | WO2007038904 | A1 | 4/2007 |
| WO | WO2010132022 | A2 | 11/2010 |
| WO | WO2020083851 | A1 | 4/2020 |
| WO | WO2020212927 | | 10/2020 |
| WO | WO2020223540 | A1 | 11/2020 |
| WO | 2021116749 | A1 | 6/2021 |

OTHER PUBLICATIONS

Related Applications Transmittal, dated Oct. 5, 2021.

YBB, YBB Professional Cup Washing Machine Tables Glass Rinser, Pitcher Rinser for Bar Café Household (Counter Top), retrieved from: https://www.amazon.com/YBB-Professional-Pitcher-Plating-Household/dp/B01MG7GPIR; Oct. 31, 2016.

Jectse, Cup Rinser, Automatic Household Commercial Cup Washer High-Pressure Cup Washer Cleaner Rinser Bar Accessories Home, Restaurant, Bar, Tea Shop, Coffee Shop, etc., Retrieved from: https://www.amazon.com/Automatic-Commercial-high-Pressure-Accessories-Restaurant/dp/B0868M9J9R, Mar. 23, 2020.

Hobart, Cleaning of Reusable Cups, Retrieved from: https://www.hobart-export.com/market-solutions/industry/cup-cleaning; Retrieved on: Sep. 23, 2021.

WebstaurantStore, Champion CG4 Low Temperature 48" Pass-Through Glass Washer, Left to Right—208/230V, Retrieved from: https://www.webstaurantstore.com/champion-cg4-low-temperature-48-pass-through-glass-washer-left-to-right-208-230v/253CG4LRV.html, Retrieved on: Sep. 23, 2021.

Northern Brewer, Vinator Bottle Rinser, Retrieved from: https://www.northernbrewer.com/products/vinator-bottle-rinser, Retrieved on Sep. 27, 2021.

Babymoov, Babymoov Turbo Pure Sterilizer & Dryer (2020), KiddiesKingdom.com, Retrieved from:https://www.kiddies-kingdom.com/health-hygiene/36070-babymoov-turbo-pure-sterilizer-dryer-2020.html, 2020.

Exair, High Efficiency Fixed Aluminum Air Amplifier, Inlet Dia.: 2.0 in, Grainger.com, Retrieved from: https://www.grainger.com/product/4LCX5?ef_id=EAIaIQobChMIotPGscCI8gIVZGxvBB3KTQnjEAQYAyABEgJDjfD_BwE:G:s&s_kwcid=AL!2966!3!281698275816!!!g!469974894180!&gucid=N:N:PS:Paid, Retrieved on: Sep. 27, 2021.

SolvAir, Food & Beverage, Retrieved from: https://www.solvair.co.uk/applications/food-and-beverage/; Retrieved on: Sep. 27, 2021.

Costway, Full-Automatic Washing Machine 7.7 lbs Washer, Retrieved from: https://www.walmart.com/ip/Full-Automatic-Washing-Machine-7-7-lbs-Washer-Spinner-Germicidal-UV-Light-Blue/354269146, Retrieved on Sep. 27, 2021.

KaTom, Perlick PKBR24 24" Underbar Glass Washer, Retrieved from: https://www.katom.com/199-PKBR24.html?gclid=EAIaIQobChMI_aLznJmE8gIV2wytBh3yjwItEAQYBSABEgLu_vD_BWE, Retrieved on Sep. 27, 2021.

Gosain, Gaurav, A More Sustainable Dishwasher, ME589: Sustainable Design, Dec. 16, 2013.

Dongguan Vistech Import & Export Co., Ltd, Mini UV Lamp Ultraviolet Germicidal Disinfection Lamp Portable UV Handheld Home Travel Ozone Sterilizer Light, Retrieved from: https://dgvistech.en.made-in-china.com/product/eZixUMaChJkH/China-Mini-UV-Lamp-Ultraviolet-Germicidal-Disinfection-Lamp-Portable-UV-Handheld-Home-Travel-Ozone-Sterilizer-Light.html, Retrieved on Sep. 30, 2021.

UVClean, UV-C Sanitizing Light Disinfection Telescoping Room Robot: Glow Trolley, Retrieved from: https://uvcleanhouse.com/products/glow-trolley, Retrieved on Sep. 30, 2021.

Meiko, Efficient Cleaning of Cups and Bottles, Retrieved from: https://www.meiko.info/en/efficient-cleaning-of-cups-and-bottles, Retrieved on Jan. 27, 2021.

Graf, Irina, United States Patent and Trademark Office, Non-Final Office Action issued in U.S. Appl. No. 17/490,879, 167 pages, dated Aug. 30, 2023.

Graf, Irina, United States Patent and Trademark Office, Non-Final Office Action issued in U.S. Appl. No. 17/490,874, 145 pages, dated Sep. 13, 2023.

Graf, Irina, United States Patent and Trademark Office, Non-Final Office Action issued in U.S. Appl. No. 17/490,869, 193 pages, dated Sep. 14, 2023.

Graf, Irina, United States Patent and Trademark Office, Notice of Allowance issued in U.S. Appl. No. 17/490,879, 25 pages, dated Feb. 16, 2024.

Graf, Irina, United States Patent and Trademark Office, Notice of Allowance issued in U.S. Appl. No. 17/490,874, 21 pages, dated Mar. 5, 2024.

Graf, Irina, United States Patent and Trademark Office, Notice of Allowance issued in U.S. Appl. No. 17/490,869, 26 pages, dated Mar. 6, 2024.

* cited by examiner

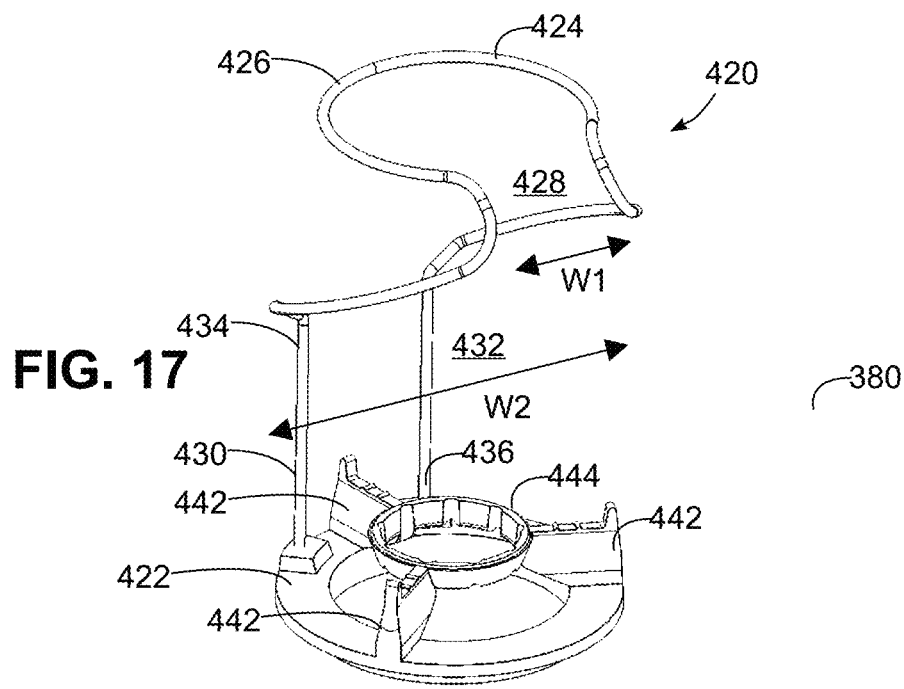
FIG. 17
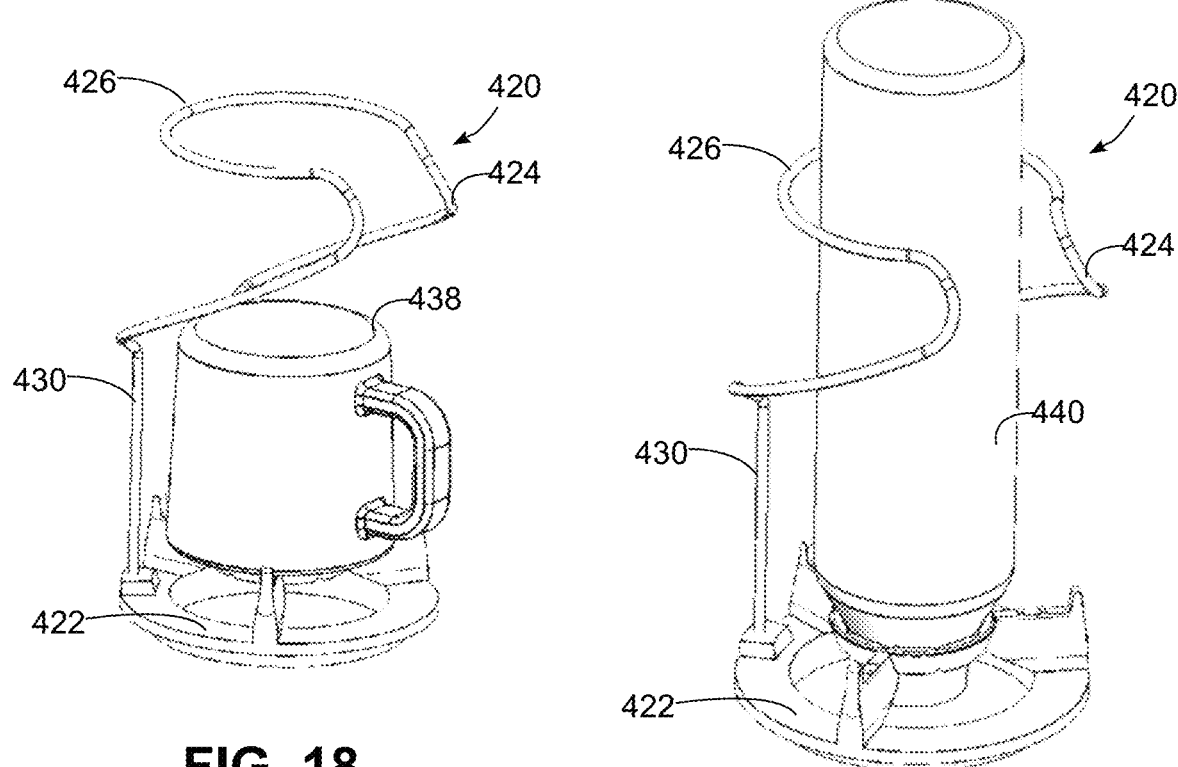
FIG. 18
FIG. 19

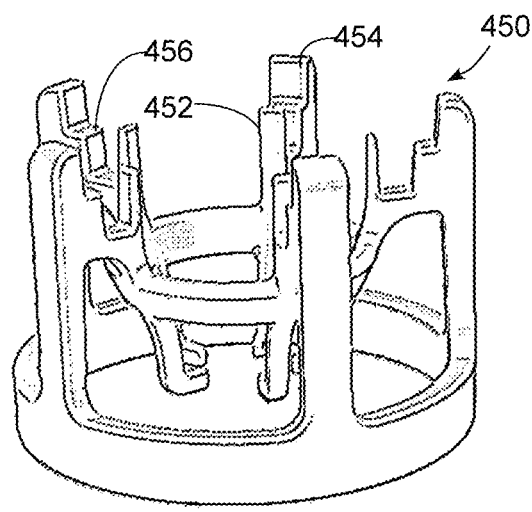
FIG. 20
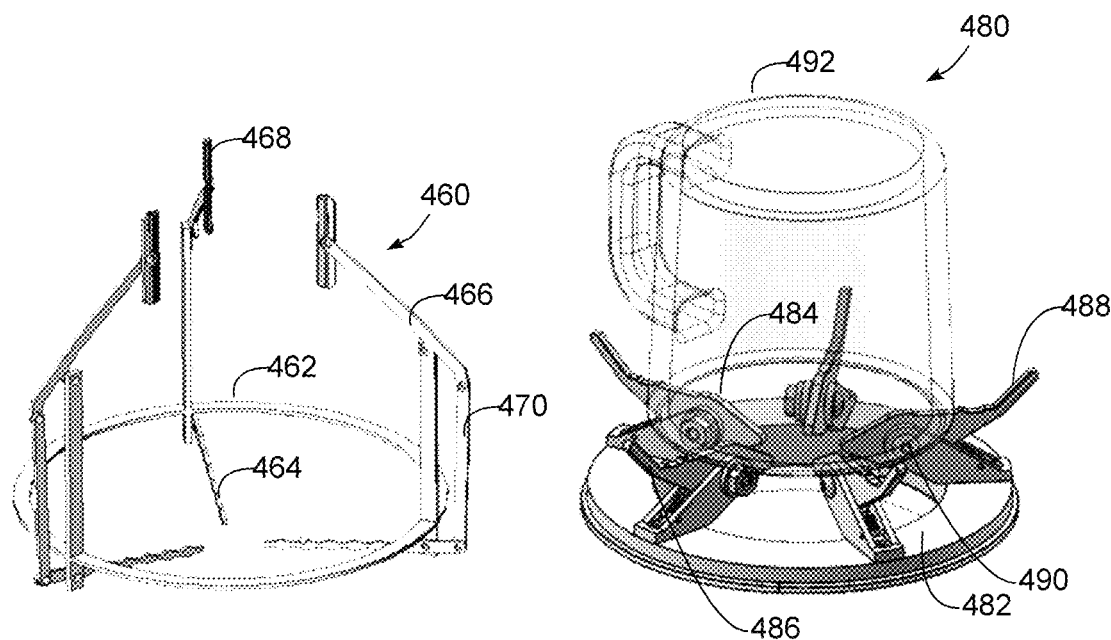
FIG. 21   FIG. 22

HIGH SPEED REUSABLE BEVERAGE CONTAINER WASHING SYSTEM WITH CONCENTRIC HOUSING MEMBERS

BACKGROUND

Due in part to the environmental concerns associated with disposable or single use beverage containers, many consumers are increasingly opting to use reusable cups, reusable bottles and other types of reusable beverage containers. In addition, some retail establishments, such as coffee shops, donut shops, and restaurants, have been willing to fill customer-provided cups and other beverage containers, and some have even introduced reusable cup programs where customers are able to purchase a reusable cup at a low initial cost when purchasing a beverage and then present that same cup at a later date for a refill.

While such programs have proven to be beneficial for both consumers and retail establishments, ensuring that the reusable cups are clean and sanitary prior to filling can be a challenge. Some municipalities, for example, have instituted ordinances that require a retail establishment to clean a work space after handling a customer-supplied reusable cup. Furthermore, pandemic-related concerns have led many retail establishments to discontinue the use of reusable cups due to the potential for a transmission of germs or contamination.

Retail establishments that serve beverages often use commercial-style dishwashers to wash cups and other utensils. Such dishwashers, however, are often configured to handle a large number of utensils in each load, and even the fastest dishwashers can still have runtimes of several minutes or more. Such dishwashers are also relatively large and noisy, and as a result are often placed in a kitchen or other area that is outside of the range of customers. As a result, traditional commercial-style dishwashers have a number of characteristics that make them generally unsuitable for use in connection with cleaning customer-provided reusable beverage containers.

Therefore, a significant need exists in the art for a system capable of washing reusable cups and other beverage containers in a fast and sanitary manner, and in particular, a system capable of being utilized in a retail establishment to clean customer-provided reusable beverage containers prior to filling, and to do so in a manner that is both fast and compatible with a fast-paced retail environment.

SUMMARY

The herein-described embodiments address these and other problems associated with the art by providing various improvements related to a beverage container washing system that may be used for rapid washing and/or sanitizing of beverage containers, e.g., for use in a retail environment to wash and/or sanitize customer-provided beverage containers prior to filling the beverage containers with purchased beverages, among other applications. Among other features, the beverage container washing system may include multiple concentric housing members supported on a base, with each having one or more openings that may be selectively aligned through driven movement of at least one of the concentric housing members to provide access to a wash chamber.

Therefore, consistent with one aspect of the invention, an apparatus for washing a beverage container may include a base, inner and outer concentric housing members supported on the base, the inner concentric housing member being disposed inwardly from the outer concentric housing member and forming at least a portion of a wash chamber, each of the inner and outer concentric housing members including an opening, a holder disposed within the wash chamber and configured to hold the beverage container during a washing operation, and a drive assembly coupled to at least one of the inner and outer concentric housing members and configured to rotate the at least one of the inner and outer concentric housing members about an axis of rotation between first and second relative positions. When in the first relative position, the respective openings of the inner and outer concentric housing members are aligned to permit external access to the holder in the wash chamber and when in the second relative position, the respective openings of the inner and outer concentric housing members are unaligned to restrict external access to the holder in the wash chamber during the washing operation.

In some embodiments, each of the inner and outer concentric housing members fully circumscribe the axis of rotation. In addition, in some embodiments, when in the first relative position, the respective openings of the inner and outer concentric housing members permit external access to the holder in the wash chamber from a first location, one of the inner and outer concentric housing members includes a second opening, and the drive assembly is further configured to rotate the at least one of the inner and outer concentric housing members to a third relative position that provides external access to the holder in the wash chamber through the second opening and from a second location that is different from the first location. Also, in some embodiments, the first and second locations are on opposite sides of the apparatus such that the beverage container may be placed within the wash chamber from the first location and removed from the wash chamber from the second location.

Moreover, in some embodiments, the drive assembly is configured to rotate the at least one of the inner and outer concentric housing members by rotating only the inner concentric housing member while the outer concentric housing member remains stationary. Further, in some embodiments, the drive assembly is configured to rotate the at least one of the inner and outer concentric housing members by rotating only the outer concentric housing member while the inner concentric housing member remains stationary. Also, in some embodiments, the drive assembly is configured to rotate the at least one of the inner and outer concentric housing members by concurrently rotating both of the inner and outer concentric housing members.

Further, in some embodiments, the inner concentric housing member includes an inner concentric dome and the outer concentric housing member includes an outer concentric dome. In some embodiments, the opening of the outer concentric dome is an entrance opening, the outer concentric dome includes an exit opening disposed on an opposite side of the outer concentric dome from the entrance opening, and the drive assembly is configured to rotate the inner concentric dome to the first relative position prior to the washing operation to align the opening of the inner concentric dome with the entrance opening to permit insertion of the beverage container into the holder in the wash chamber, to rotate the inner concentric dome to the second relative position proximate a start of the washing operation to inhibit wash fluid sprayed during the washing operation from exiting through the entrance and exit openings of the outer concentric dome, and to rotate the inner concentric dome to a third relative position proximate an end of the washing operation to align the opening of the inner concentric dome with the exit opening to permit removal of the beverage container from the holder in the wash chamber.

Also, in some embodiments, the opening of the outer concentric dome is an entrance opening, the outer concentric dome includes an exit opening disposed on an opposite side of the outer concentric dome from the entrance opening, the opening in the inner concentric dome is a first opening and the inner concentric dome includes a second opening disposed on an opposite side of the inner concentric dome from the first opening, and the drive assembly is configured to rotate the inner concentric dome to the first relative position prior to the washing operation to align one of the first and second openings of the inner concentric dome with the entrance opening to permit insertion of the beverage container into the holder in the wash chamber, to rotate the inner concentric dome to the second relative position proximate a start of the washing operation to inhibit wash fluid sprayed during the washing operation from exiting through the entrance and exit openings of the outer concentric dome, and to rotate the inner concentric dome to a third relative position proximate an end of the washing operation to align one of the first and second openings of the inner concentric dome with the exit opening to permit removal of the beverage container from the holder in the wash chamber.

In some embodiments, the holder is disposed in a fixed location within the wash chamber and the base includes a collector configured to collect the wash fluid sprayed during the washing operation. Some embodiments may also include a spray assembly including at least one sprayer disposed within the wash chamber and configured to spray the wash fluid onto the beverage container while the beverage container is held by the holder, with the at least one sprayer is supported by the base. Some embodiments may further include an ultraviolet sanitizing assembly including at least one ultraviolet light disposed within the wash chamber and configured to emit ultraviolet light toward the beverage container while the beverage container is held by the holder. In some embodiments, the at least one ultraviolet light is supported by and rotatable with the inner concentric dome. Further, in some embodiments, the at least one ultraviolet light is stationary and supported by the outer concentric dome. In addition, some embodiments may further include a dryer assembly including at least one air outlet disposed in the inner concentric dome and configured to blow air onto the beverage container while the beverage container is held by the holder.

In addition, in some embodiments, the drive assembly includes an electric motor and a first gear, and the inner concentric dome includes a second gear circumscribing a perimeter of the inner concentric dome and engaging the first gear. Some embodiments may also include a position detector configured to detect one or more relative positions between the inner and outer concentric housing members about the axis of rotation, and a controller coupled to the drive assembly and the position detector and configured to control the drive assembly to rotate the at least one of the inner and outer concentric housing members between the first and second relative positions based at least in part on an output of the position detector.

Consistent with another aspect of the invention, an apparatus for washing a beverage container may include a base including a drain configured to collect wash fluid sprayed during a washing operation, inner and outer concentric domes supported on the base, the inner concentric dome being disposed inwardly from the outer concentric dome and forming at least a portion of a wash chamber with the base, the inner concentric dome including an opening and the outer concentric dome including an entrance opening and an exit opening, a holder disposed within the wash chamber and configured to hold the beverage container during the washing operation, a spray assembly including at least one sprayer disposed within the wash chamber and configured to spray the wash fluid onto the beverage container while the beverage container is held by the holder, a drive assembly coupled to the inner concentric dome and configured to rotate the inner concentric dome about an axis of rotation, and a controller coupled to the drive assembly. The controller is configured to control the drive assembly to rotate the inner concentric dome to a first relative position prior to the washing operation to align the opening of the inner concentric dome with the entrance opening to permit insertion of the beverage container into the holder in the wash chamber, thereafter rotate the inner concentric dome to a second relative position proximate a start of the washing operation to inhibit wash fluid sprayed during the washing operation from exiting through the entrance and exit openings of the outer concentric dome, and rotate the inner concentric dome to a third relative position proximate an end of the washing operation to align the opening of the inner concentric dome with the exit opening to permit removal of the beverage container from the holder in the wash chamber.

Consistent with yet another aspect of the invention, an apparatus for washing a beverage container may include a base including a drain configured to collect wash fluid sprayed during a washing operation, inner and outer concentric domes supported on the base, the inner concentric dome being disposed inwardly from the outer concentric dome and forming at least a portion of a wash chamber with the base, the inner concentric dome including first and second openings and the outer concentric dome including an entrance opening and an exit opening, a holder disposed within the wash chamber and configured to hold the beverage container during the washing operation, a spray assembly including at least one sprayer disposed within the wash chamber and configured to spray the wash fluid onto the beverage container while the beverage container is held by the holder, a drive assembly coupled to the inner concentric dome and configured to rotate the inner concentric dome about an axis of rotation, and a controller coupled to the drive assembly. The controller is configured to control the drive assembly to rotate the inner concentric dome to a first relative position prior to the washing operation to align one of the first and second openings of the inner concentric dome with the entrance opening to permit insertion of the beverage container into the holder in the wash chamber, thereafter rotate the inner concentric dome to a second relative position proximate a start of the washing operation to inhibit wash fluid sprayed during the washing operation from exiting through the entrance and exit openings of the outer concentric dome, and rotate the inner concentric dome to a third relative position proximate an end of the washing operation to align one of the first and second openings of the inner concentric dome with the exit opening to permit removal of the beverage container from the holder in the wash chamber.

These and other advantages and features, which characterize the invention, are set forth in the claims annexed hereto and forming a further part hereof. However, for a better understanding of the invention, and of the advantages and objectives attained through its use, reference should be made to the Drawings, and to the accompanying descriptive matter, in which there is described example embodiments of the invention. This summary is merely provided to introduce a selection of concepts that are further described below in the detailed description, and is not intended to identify key or essential features of the claimed subject matter, nor is it intended to be used as an aid in limiting the scope of the claimed subject matter.

BRIEF DESCRIPTION OF THE DRAWINGS

FIG. 17 is a perspective view of an alternate holder to that of FIG. 13.

FIG. 18 illustrates a mug held by the holder of FIG. 17.

FIG. 19 illustrates a bottle held by the holder of FIG. 17.

FIGS. 20-23 are perspective views of additional alternate holders to that of FIG. 13.

DETAILED DESCRIPTION

Figure 1:
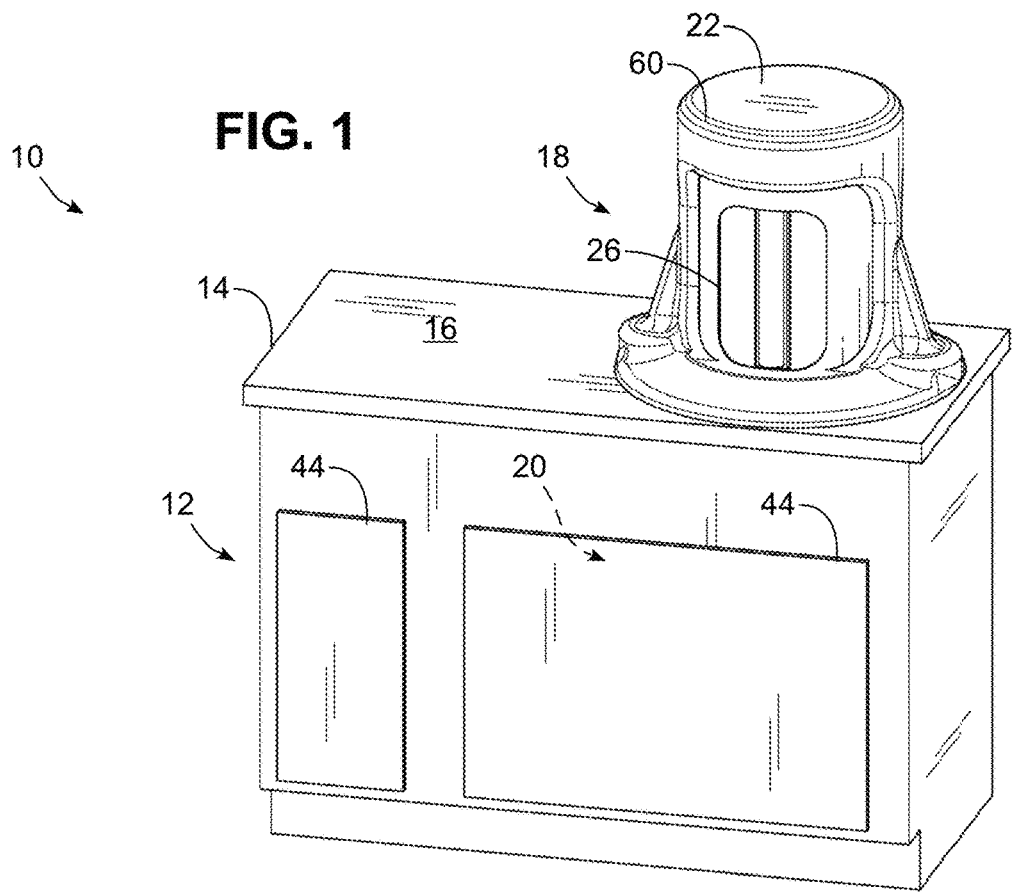
FIG. 1 is a perspective view of a beverage container washing system consistent with some embodiments of the invention.

In some embodiments consistent with the invention, a beverage container washing system may be used to rapidly wash beverage containers, including, for example, reusable beverage containers such as may be provided by customers of a retail establishment.

A beverage container, in this regard, may be considered to be any type of container that is capable of holding a beverage for consumption, including, for example, a cup, a bottle, a bowl, etc. A beverage container may generally include a mouth or opening defined by a lip, and may or may not include a cap, a lid or other form of closure. A beverage container may be reusable to the extent that the beverage container may be reused multiple times, in contrast with a disposable or single use beverage container that is generally thrown away after use.

A beverage container washing system consistent with some embodiments of the invention may be used to wash or clean a beverage container. In some embodiments, a beverage container washing system may also be considered to be a sanitizing system that is also capable of sanitizing a beverage container to inactivate, reduce or destroy microorganisms on the surface of the beverage container, e.g., bacteria and other pathogenic organisms. Sanitization may be achieved through the use of high temperatures, ultraviolet irradiation, disinfecting agents, or some combination of the same, such that a sanitizing operation may be considered to be a particular type of washing operation where some degree of sanitization occurs in addition to washing or cleaning. It will be appreciated, however, that some of the concepts disclosed herein may be utilized in connection with washing systems that, while capable of washing or cleaning a beverage container, are not considered to sanitize the beverage container to the extent required to consider the beverage container as being sanitized at the completion of a washing operation.

It will also be appreciated that a beverage container washing system consistent with the invention may be, but is not necessarily, used in a retail environment (e.g., a bar, a coffee shop, a restaurant, etc.) to rapidly wash the beverage container of a customer prior to filling the beverage container with a beverage that has been purchased by a customer, e.g., in some instances, less than one minute, and in some instances, about 30 seconds or less. Further, a beverage container washing system consistent with the invention may be, but is not necessarily, used to rapidly wash a single, individual beverage container in a washing operation. In other embodiments, for example, some of the concepts disclosed herein may be utilized in non-retail environments, including within a consumer's home, an office environment, or any other environment for which it may be desired to wash beverage containers. Further, even within a retail environment, a washing system consistent with the invention may be used in non-customer facing applications, e.g., behind the counter, in the kitchen, etc. Further, some of the concepts disclosed herein may be adapted for use in connection with washing multiple beverage containers in a single washing operation, as well as washing operations that take one or more minutes to complete.

In the example embodiment discussed hereinafter, hot water (e.g., about 150 degrees/65 degrees Celsius or higher in some embodiments, or about 165 degrees Fahrenheit/74 degrees Celsius or higher in some embodiments), high pressure (e.g., about 100 psi or greater), high speed air for drying, and ultraviolet irradiation are used to rapidly wash and sanitize an individual beverage container, e.g., in about 30 seconds, and do so in a manner that has a minimal countertop space presence. Furthermore, in order to minimize interaction between a customer and retail establishment employee, separate entrance and exit openings are used, such that the opening in which a customer inserts an unwashed beverage container into the system prior to performing a washing operation is different from the opening in which a retail establishment employee removes the washed beverage container at the completion of the washing operation. A washing system consistent with the invention may, in some instances, move the beverage container between multiple stations to perform different actions, and in some instances, operate on different beverage containers concurrently in different stations. In other instances, a washing system consistent with the invention may perform all of the actions associated with a washing operation while the beverage container is maintained in the same location. It will be appreciated, however, that in other embodiments, a washing system consistent with the invention may use the same opening for insertion and removal of a beverage container, and may operate on multiple beverage containers at the same time. Further, in some embodiments, lower temperatures and/or pressures may be used, and ultraviolet irradiation and/or drying may be omitted, or additional actions, such as the introduction of detergents, disinfecting agents, etc. may be used. Therefore, the invention is not limited to the specific embodiments disclosed herein.

Now turning to the drawings, wherein like parts are denoted by like numbers throughout the several views, FIG. 1 illustrates a beverage container washing system or apparatus 10 consistent with some embodiments of the invention, and suitable for installation, for example, in a cabinet 12 that forms a counter 14 in a retail establishment. In the illustrated embodiment, washing system 10 may also be considered to be a sanitizing system 10 due to the use of hot water and/or ultraviolet irradiation, so these terms may be used interchangeably. It will be appreciated, however, that the reference to a particular concept used in a sanitizing system or in connection with a sanitizing operation does not necessarily mean that the concept cannot also be used in washing system or in connection with washing operations that are not necessarily considered sufficient for full sanitization of a beverage container.

Counter 14 includes a countertop 16, and washing system 10 includes a countertop portion 18 that projects above countertop 16 and an undercounter portion 20 that is predominantly mounted within cabinet 12 to minimize the amount of countertop space occupied by countertop portion 18. In other embodiments, washing system 10 may be fully implemented in a countertop, standalone or undercounter configuration, so the invention is not limited to the particular combination of countertop and undercounter portions as illustrated herein. In some embodiments, the countertop portion may be fixed to a countertop, but he undercounter portion may be separated, or may be mounted on a cart to simplify installation and service.

Figure 2:
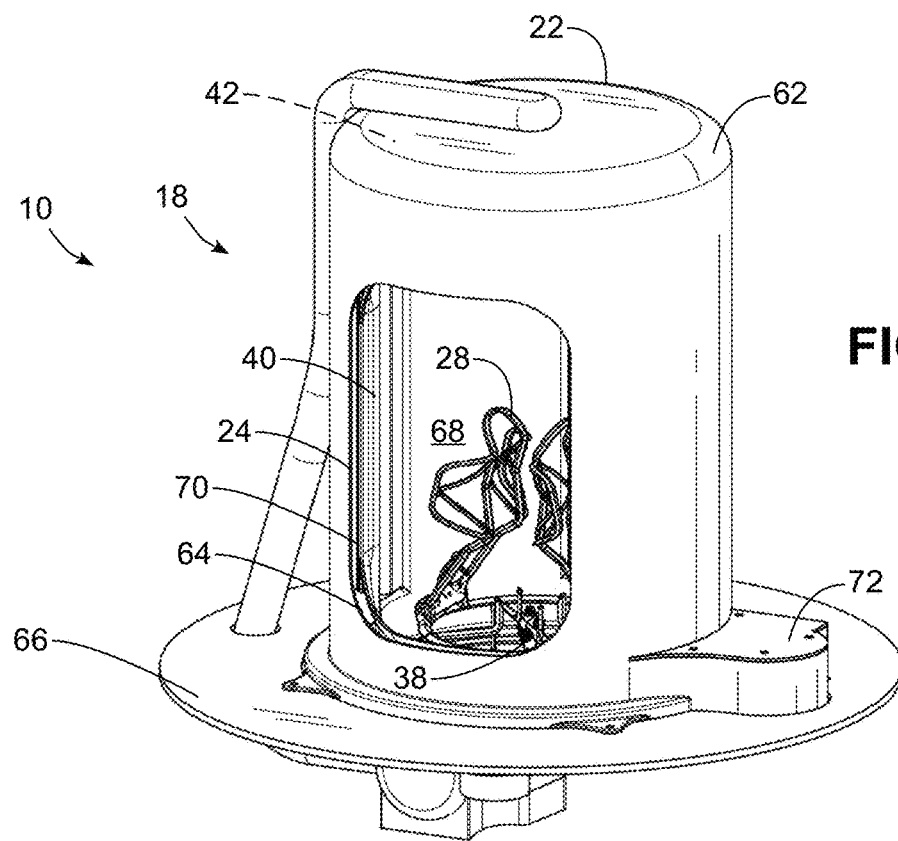
FIG. 2 is a perspective view of an opposite side of a countertop portion of the beverage container washing system of FIG. 1.

With additional reference to FIG. 2, which shows an opposite side of countertop portion 18 of washing system 10, the countertop portion 18 generally includes a housing 22 having a pair of openings 24, 26, with opening 24 operating as an entrance through which a beverage container is inserted or received prior to performing a washing operation and opening 26 operating as an exit through which a beverage container is accessed or removed after performing a washing operation. Through the use of separate openings 24, 26, handling of unwashed beverage containers by retail establishment employees may be reduced or eliminated. In other embodiments, however, a single entrance/exit opening may be used.

Countertop portion 18 also includes a holder 28 that is disposed within housing 22 and is configured to hold a beverage container during a washing or sanitizing operation. In addition, and with additional reference to FIG. 3, a number of assemblies 30, 32, 34 are also utilized for performing various actions on the beverage container during a washing or sanitizing operation, and are controlled by a controller 36, which will be discussed in greater detail below.

First, a spray assembly 30, including one or more sprayers (e.g., sprayer 38 as shown in FIG. 2) is disposed within housing 22 and configured to spray a wash fluid onto the beverage container while the beverage container is held by holder 28. The wash fluid may be water in some instances, while in other instances, the wash fluid may include various agents such as detergents, disinfecting agents, etc. As will become more apparent below, when sanitization is desired, the wash fluid sprayed by the spray assembly 30 may be heated to a sanitizing temperature, e.g., about 150 degrees Fahrenheit or higher in some embodiments, and about 165 degrees Fahrenheit or higher in some embodiments, and in some instances may be pressurized at a high pressure, e.g., about 100 psi or above. Second, an ultraviolet sanitizing assembly 32, including one or more ultraviolet lights 40 (one of which is shown in FIG. 2), is disposed within housing 22 and configured to emit ultraviolet light toward the beverage container while the beverage container is held by holder 28. Third, a dryer assembly 34, e.g., including one or more air outlets 42, is disposed within housing 22 and configured to blow air onto the beverage container while the beverage container is held by holder 28. A number of other components in each of these assemblies, as noted above, may be disposed within cabinet 12, and may be accessed, for example, through one or more cabinet doors 44 (FIG. 1).

Figure 3:
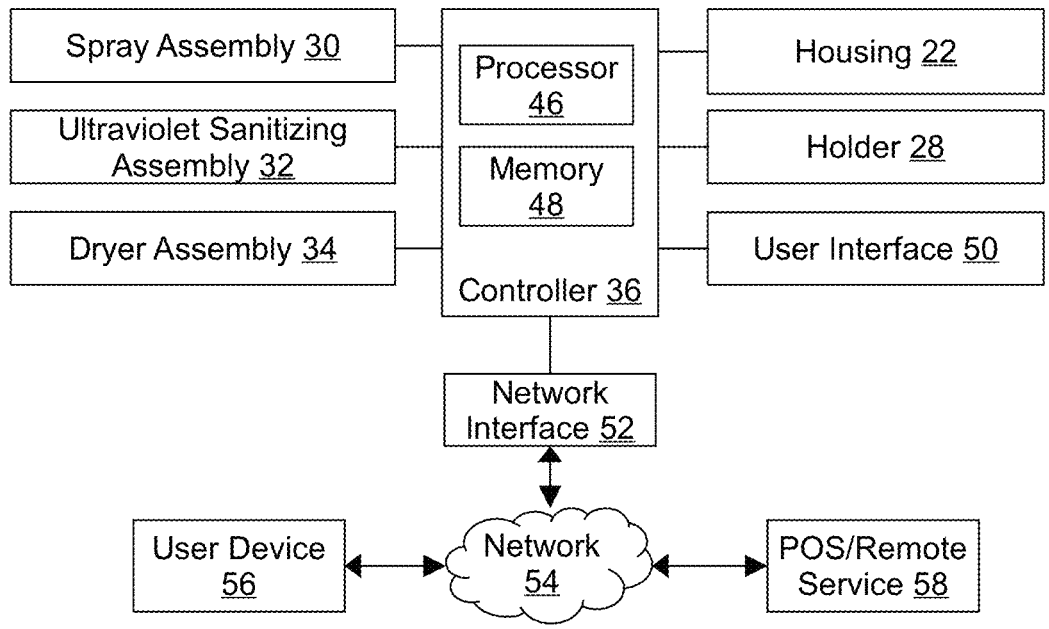
FIG. 3 is a block diagram of an example control system for the beverage container washing system of FIG. 1.

Now turning specifically to FIG. 3, washing system 10 may be under the control of a controller 36 that receives inputs from a number of components and drives a number of components in response thereto. Controller 36 may, for example, include one or more processors 46 and a memory 48 within which may be stored program code for execution by the one or more processors 46. The memory may be embedded in controller 36, but may also be considered to include volatile and/or non-volatile memories, cache memories, flash memories, programmable read-only memories, read-only memories, etc., as well as memory storage physically located elsewhere from controller 36, e.g., in a mass storage device or on a remote computer interfaced with controller 36. Controller 36 may also be implemented as a microcontroller in some embodiments, and as such these terms are used interchangeably herein. Controller 36 may also include discrete circuit logic in some embodiments, e.g., including passive and/or active circuit components.

As shown in FIG. 3, controller 36 may be interfaced with various components, including a spray assembly 30, ultraviolet sanitizing assembly 32, and dryer assembly 34, as well as housing 22 and/or holder 28. In addition, one or more user interfaces 50, e.g., including various input/output devices such as knobs, dials, sliders, switches, buttons, lights, textual and/or graphics displays, touch screen displays, speakers, image capture devices, microphones, etc., may be used for receiving input from and communicating with one or more users. Separate user controls and/or displays may be provided, for example, on or near housing 22 for a customer and a retail establishment employee (e.g., to start or stop a washing operation), and in some instances, additional controls and/or displays may be provided at different locations, e.g., under countertop 16 or behind a cabinet door 44, to perform additional operations, such as initializing and/or shutting off the system, flushing the system, displaying error conditions, etc.

In some embodiments, controller 36 may also be coupled to one or more network interfaces 52, e.g., for interfacing with external devices via wired and/or wireless networks 54 such as Ethernet, Bluetooth, NFC, cellular and other suitable networks. It may be desirable, for example, to interface with one or more user devices 56, e.g., a customer's mobile phone, to enable a customer to start a washing operation, in some instances in connection with ordering and/or paying for a beverage. It may also be desirable to interface with various backend devices such as a point of sale (POS) system and/or a remote service 58. Moreover, in some embodiments, at least a portion of controller 36 may be implemented externally, e.g., within a mobile device, a cloud computing environment, etc., such that at least a portion of the functionality described herein is implemented within the portion of the controller that is externally implemented.

In some embodiments, controller 36 may operate under the control of an operating system and may execute or otherwise rely upon various computer software applications, components, programs, objects, modules, data structures, etc. In addition, controller 36 may also incorporate hardware logic to implement some or all of the functionality disclosed herein. Further, in some embodiments, the sequences of operations performed by controller 36 to implement the embodiments disclosed herein may be implemented using program code including one or more instructions that are resident at various times in various memory and storage devices, and that, when read and executed by one or more hardware-based processors, perform the operations embodying desired functionality. Moreover, in some embodiments, such program code may be distributed as a program product in a variety of forms, and that the invention applies equally regardless of the particular type of computer readable media used to actually carry out the distribution, including, for example, non-transitory computer readable storage media. In addition, it will be appreciated that the various operations described herein may be combined, split, reordered, reversed, varied, omitted, parallelized and/or supplemented with other techniques known in the art, and therefore, the invention is not limited to the particular sequences of operations described herein.

As noted above, controller 36 may be interfaced in some embodiments with one or both of housing 22 and holder 28. In the embodiment illustrated in FIGS. 1-2, for example, washing system 10 includes a concentric housing arrangement, also referred to herein as a concentric dome arrangement, whereby housing 22 includes an outer decorative cover 60 coupled with a pair of concentric housing members or domes 62, 64 supported by a base 66. Concentric housing member or dome 62 is an outer concentric housing member or dome while concentric housing member or dome 64 is an inner concentric housing member or dome that is disposed inwardly from outer concentric housing member or dome 62 and forms at least a portion of a wash chamber 68 with the base. Entrance opening 24 and exit opening 26 are defined in outer concentric housing member 62 while an additional opening 70 is provided in inner concentric housing member 64, and a drive motor 72 is used to rotate inner concentric housing member 64 to selectively move opening 70 between a loading position where opening 70 is aligned with entrance opening 24 to provide access to the wash chamber for insertion of the beverage container prior to a washing operation, a washing position where opening 70 is intermediate entrance and exit openings 24, 26 (thereby closing both openings), and an unloading position where opening 70 is aligned with exit opening 26 to provide access to the wash chamber for removal of the beverage container at the completion of a washing operation.

In other embodiments, however, no mechanical manipulation of a housing may be used, whereby controller 36 may not be electronically coupled to housing 22. For example, it may be desirable in some embodiments to keep an entrance opening and an exit opening open at all times, or to use a door or other manually or mechanically actuated closure.

In the illustrated embodiment of FIGS. 1 and 2, holder 28 may be fixed in location and thus no electronic coupling between controller 36 and holder 28 may be used. In other embodiments, however, it may be desirable to configure holder 28 to electronically open or close, rotate, and/or move, including moving between different stations, so controller 36 may be electronically coupled to holder 28 in some embodiments.

Figure 4:
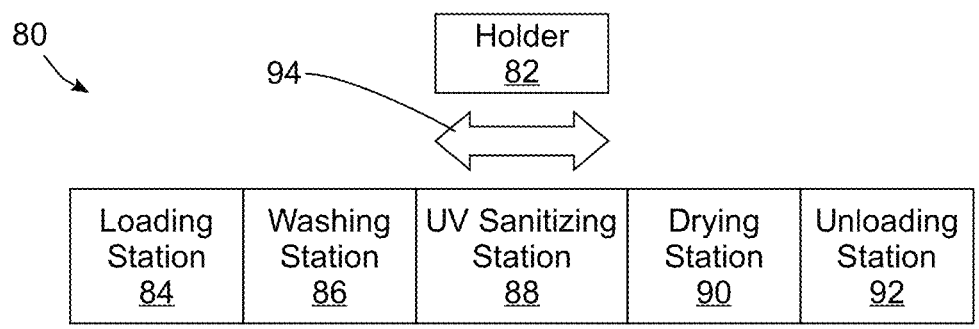
FIG. 4 is a block diagram of an alternate beverage container washing system to that of FIG. 1.

For example, as illustrated by washing system 80 of FIG. 4, a holder 82 may be moved between different stations, e.g., a loading station 84, a washing station 86, an ultraviolet sanitizing station 88, a drying station 90 and/or an unloading station 92, e.g., by a conveyor 94 or other articulating configuration. Further, in some embodiments, multiple actions may be performed at the same station (e.g., drying and exposing to ultraviolet radiation in the same station), or multiple stations may perform different aspects of a particular action (e.g., separate wash and rinse stations).

Figure 5:
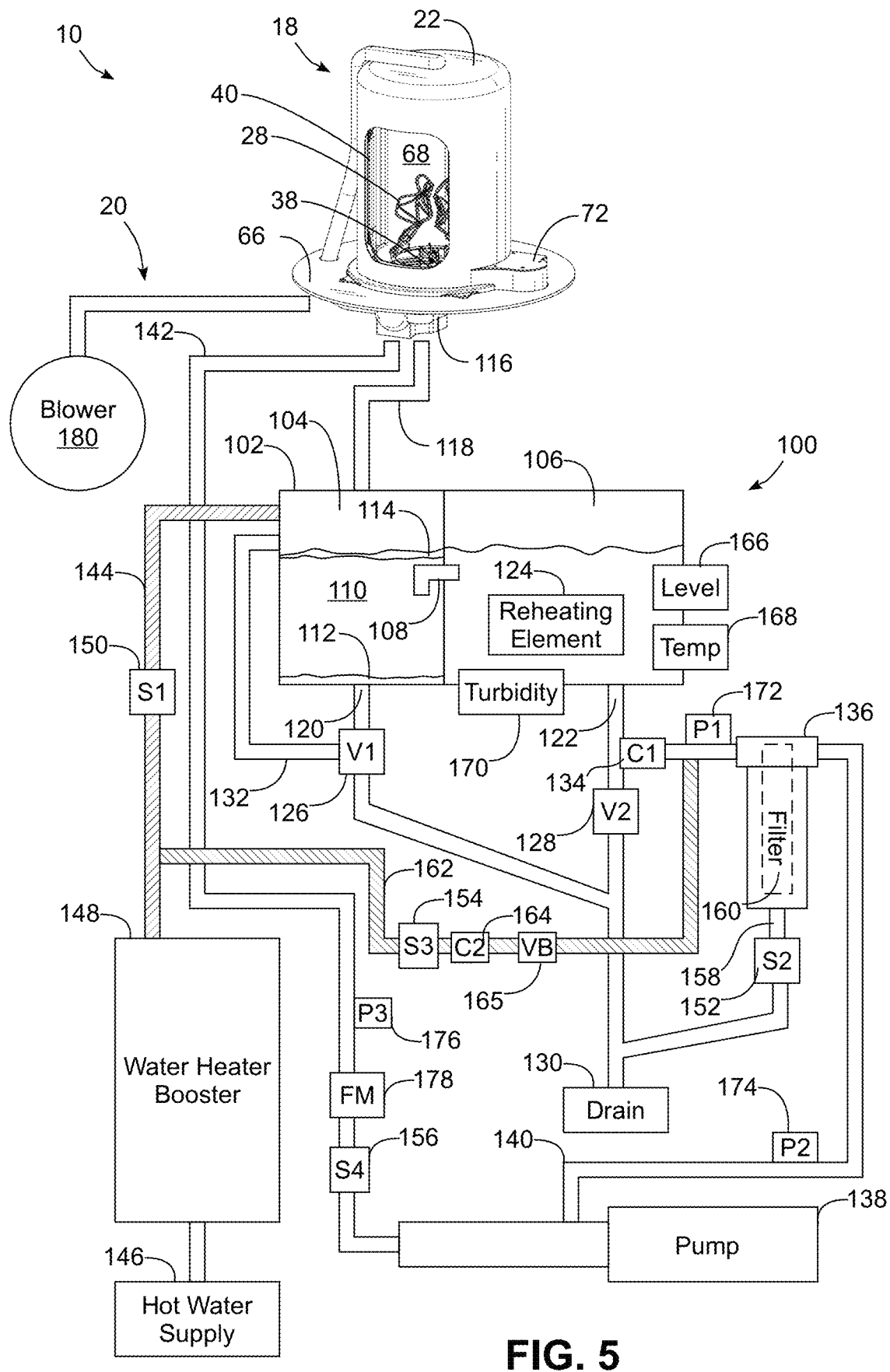
FIG. 5 is a block diagram of an undercounter portion of the beverage container washing system of FIG. 1.

Now turning to FIG. 5, and as discussed above, beverage container washing system 10 includes a number of additional components, many of which are in an undercounter portion 20, that operate each of spray assembly 30, ultraviolet sanitizing assembly 32 and dryer assembly 34. Spray assembly 30, for example, additionally includes a wash fluid recirculation assembly 100 that is disposed in cabinet 12 and underneath countertop 16 and is in fluid communication with sprayer 38 through countertop 16.

In particular, in the illustrated embodiment, it is desirable to recirculate wash fluid for use in multiple washing operations to reduce overall water and energy consumption. Rather than utilizing fresh water for each washing operation, the wash fluid may be reused for multiple washing operations, and in some instances, one or more fluid property sensors (e.g., a turbidity sensor and/or a conductivity sensor) may be used to monitor the state of the wash fluid and periodically perform a wash fluid refresh operation to drain at least a portion of the wash fluid to a drain and replace the removed portion with fresh water (referred to herein as make up water).

Wash fluid recirculation assembly 100, in particular, includes a tank 102 including first and second chambers 104, 106 with a cross-over 108 that fluidly couples first and second chambers 104, 106 to one another. First chamber 104 is generally used to house black water, while second chamber 106 is used to generally house grey water. Cross-over 108 may be implemented as an inverted conduit that is disposed below the fluid level of the wash fluid 110 disposed in tank 102, which generally reduces the amount of solid particles 112 (which generally fall to the bottom of first chamber 104 and thus below the inlet of the inverted conduit) and floating particles 114 (which generally float in first chamber 104 and thus above the inlet of the inverted conduit) that are drawn into second chamber 106. A collector 116 in base 66 of housing 22 collects wash fluid sprayed by sprayer 38, and the collected wash fluid is conveyed by a collector line 118 to first chamber 104 of tank 102.

Each chamber 104, 106 has an associated drain or outlet 120, 122, and tank 102 further includes a heater 124, e.g., a reheating element, that maintains the temperature of wash fluid 110 above the desired sanitizing temperature. Respective drain devices such as dump valves 126, 128 (also referred to as valves V1 and V2) are coupled to outlets 120, 122 and feed to a drain 130, e.g., in the building plumbing system. Dump valve 126 in some embodiments may also include an overflow line 132 to collect wash fluid when the fluid level rises above a predetermined level. In some embodiments, drain devices other than valves may be used in other embodiments, e.g., drain pumps, and in some embodiments, overflow may be controlled by a separate float that activates a drain pump.

A check valve 134 (also denoted as C1) is coupled between outlet 122 and dump valve 128 to route wash fluid to a filter 136 and then onward to a pump 138 through a recirculation line 140, and pump 138 pressurizes the wash fluid (e.g., to a pressure about 100 psi or above in some embodiments, and in some embodiments about 150 psi or above) and outputs the pressurized wash fluid to sprayer 38 through a sprayer supply line 142. In some embodiments, pump 138 may be a multi-stage pump, e.g., 1 hp, 17-stage pump. During a washing operation, wash fluid in the second chamber 106 of tank 102 is thus drawn out of outlet 122 and through filter 136 by pump 138, and then pressurized and supplied to sprayer 38 by pump 138. The wash fluid emitted by sprayer 38 is then collected in collector 116 of base 66 and returned to first chamber 104 of tank 102.

Fresh or make up water is supplied to tank 102 by a make up water line 144. In order to supply the fresh or make up water at a suitable temperature for washing or sanitizing operations, fresh water from a hot water supply 146 (e.g., output by a building water heater) may first be passed through a water heater booster 148, which maintains a quantity of water at an elevated temperature (e.g., about 150 degrees Fahrenheit or higher in some embodiments, and about 165 degrees Fahrenheit or higher in some embodiments). In other embodiments, however, fresh water may be supplied from a cold water supply and heated by water heater booster, and in some embodiments, water heater booster 148 may be omitted, with the temperature of the wash fluid in tank 102 predominantly controlled by reheating element 124.

Four additional valves, e.g., solenoid valves 150, 152, 154 and 156 (also denoted respectively as valves S1-S4), may also be incorporated into assembly 100. Valve 150 is a make up water valve, and is provided in make up water line 144 to control the supply of make up water to first chamber 104 of tank 102. Valve 156 is disposed in sprayer supply line 142, and is actuated when pump 138 is actuated to supply wash fluid to sprayer 38.

In addition, in the illustrated embodiment, filter 136 is a flushable filter and includes a second, cleanout outlet 158, and valve 152 is configured as a cleanout valve that couples cleanout outlet 158 to drain 130. Valve 154 in turn is configured as a filter clean valve that is coupled to make up water line 144 to supply fresh water to recirculation line 140 upstream of a filter element 160 of filter 136 through a fresh water supply line 162. It will be appreciated that when valves 152, 154 are closed and pump 138 is running wash fluid from tank 102 flows through an upstream portion of recirculation line 140, through filter element 160, and through the first outlet of the filter and a downstream portion of the recirculation line 140 to pump 138. However, whenever it is desirable to perform a filter cleaning operation (generally while pump 138 is shut off), valves 152 and 154 may be opened to supply fresh water to an outside or upstream side of the filter element 160 and then out cleanout outlet 158 to run fresh water over the outside of the filter element and flush any debris on the filter element into drain 130. In addition, in some embodiments, a check valve 164 (also denoted as C2) and a vacuum breaker 165 may also be provided in fresh water supply line 162 to inhibit reverse fluid flow to the make up water line 144. In other embodiments, gray water may be used to clean the filter, e.g., by coupling line 162 to an outlet of pump 138 instead of to a fresh water source, e.g., between pump 138 and valve 156, and with an additional valve controlling fluid flow through line 162.

Assembly 100 may also include a number of sensors to monitor the operation of the assembly and initiate various actions in response thereto. A fluid level sensor 166 may be disposed in tank 102 to sense a fluid level therein, and the controller may utilize the output of this sensor to control make up water valve 150 to maintain a desired fluid level in the tank. A temperature sensor 168 may be disposed in tank 102 to sense the wash fluid temperature, and the controller may utilize the output of this sensor to control reheating element 124 to regulate the wash fluid temperature in the tank. One or more fluid property sensors, e.g., a turbidity sensor 170, a conductivity sensor, and/or another sensor suitable for measuring various fluid properties, may also be disposed in tank 102, e.g., in second chamber 106, or otherwise disposed elsewhere in assembly 100, to sense the water quality and/or cleanliness of the wash fluid, and the controller may utilize the output of this sensor to trigger a wash fluid refresh operation that drains at least a portion of the wash fluid to drain 130 and adds fresh water to tank 102.

A pair of pressure sensors 172, 174 (also denoted as P1 and P2) may also be disposed upstream and downstream of filter element 160 (e.g., within upstream and downstream portions of recirculation line 140), and the controller may utilize the outputs of these sensors to sense a pressure differential indicative of a dirty or clogged filter element, and thereby trigger a filter cleaning operation. An additional pressure sensor 176 (also denoted as P3) and a flowmeter 178 may also be disposed downstream of pump 138, e.g., in sprayer supply line 142, and the controller may use the outputs of these sensors to monitor the supply of wash fluid to sprayer 38. As will also be discussed in greater detail below, a dryer assembly may also include one or more blowers, e.g., a blower 180, that supply air to one or more air knives.

Figure 6:
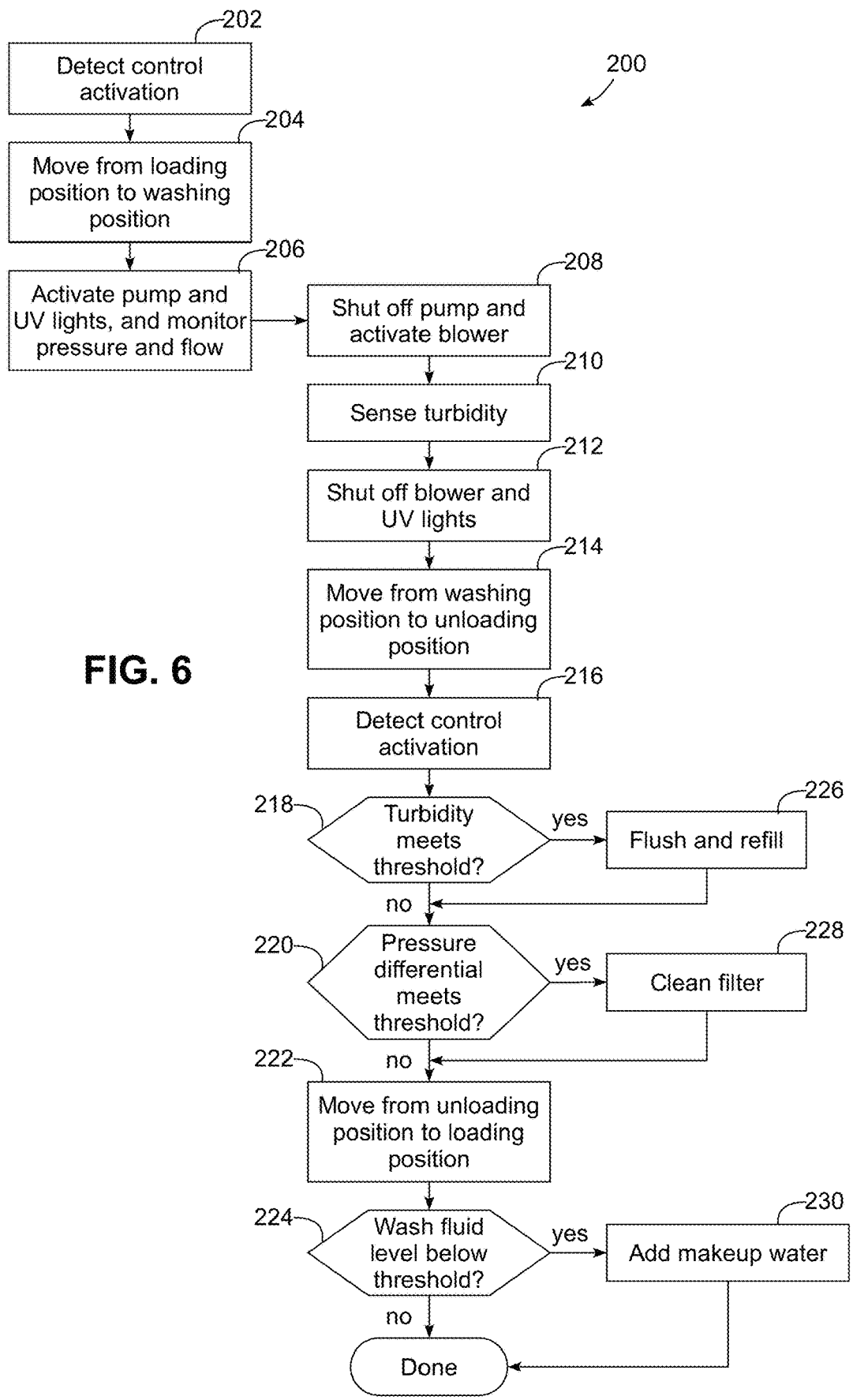
FIG. 6 is a flowchart illustrating an example sequence of operations for a washing operation performed by the beverage container washing system of FIG. 1.

FIG. 6 next illustrates an example sequence of operations 200 capable of being performed by controller 36 of beverage container washing system 10 to perform washing operations in a manner consistent with some embodiments of the invention. It is assumed that washing system 10 includes three positions, a loading position where the washing system is configured to allow a customer to insert a beverage container into the holder in the wash chamber (e.g., through entrance opening 24 of FIG. 2), a washing position where the washing system is configured to perform a washing operation (e.g., with entrance and exit openings 24, 26 closed), and an unloading position where the washing system is configured to allow an employee to remove a beverage container from the holder in the wash chamber (e.g., through exit opening 26 of FIG. 1). It is also assumed that at the beginning of sequence 200, the washing system 10 is in the loading position, and a customer has inserted a beverage container into the holder in the wash chamber. In addition, it will be appreciated that during this time, reheating element 124 (e.g., as a result of a background process executing in a controller, or in a dedicated circuit) may also be cycled to maintain the fluid temperature in the tank at a desired level.

Sequence 200 may be initiated, for example, in response to selection of a "start" control by a customer or employee, e.g., on a physical user interface provided on the washing system, via a foot pedal or switch, via a gesture or audible command, on a display of a POS system, on an app running on a mobile device, or another suitable manner for starting a washing operation. In block 202, activation of the control is detected, and in block 204, the washing system is moved from the loading position to the washing position (e.g., by rotating inner concentric housing member 64 with drive motor 72).

Next, in block 206, the pump of the spray assembly and the UV lights of the ultraviolet sanitizing assembly are activated to initiate spraying of the beverage container by sprayer 38 and irradiation of the beverage container with ultraviolet light (in another embodiment, the spray assembly and UV lights may be activated sequentially rather than concurrently). In addition, during this time pressure sensors 172-176 and flowmeter 178 are monitored to track the output flow of pump 138, as well as to monitor the pressure differential on the upstream and downstream sides of filter 136.

After some period of time, the pump is shut off and blower 180 of the dryer assembly is activated in block 208 to transition between washing the beverage container and drying the beverage container. Then, in block 210, the turbidity (or another property of the wash fluid) is sensed using sensor 170, and thereafter, the blower and UV lights are shut off in block 212, whereby the washing or sanitizing operation is complete.

Next, in block 214, the washing system is moved from the washing position to the unloading position (e.g., by rotating inner concentric housing member 64 with drive motor 72) to enable the beverage container to be removed from the holder in the wash chamber. Confirmation of removal of the beverage container is obtained in block 216 by detecting activation of an appropriate control (e.g., the same control used to start the washing operation in block 202 or a different control). Blocks 218 and 220 then determine whether conditions were detected indicating the need for either or both of a wash fluid refresh operation and a filter clean operation, and if neither operation is needed, control passes to block 222 to move the washing system from the unloading position to the loading position (e.g., by rotating inner concentric housing member 64 with drive motor 72) to prepare the washing system for a next washing operation. It will be appreciated that in embodiments where the loading and unloading positions are the same, block 222 may be omitted. Block 224 then determines, e.g., using fluid level sensor 166, whether the wash fluid level in the tank is below a threshold (e.g., where the wash fluid level has dropped below a minimum level), and assuming not, performance of sequence 200 is complete.

Returning to block 218, this block determines whether a need exists for a wash fluid refresh operation by determining if the turbidity sensed in block 210 (or another sensed fluid property) meets a threshold, e.g., where the turbidity of the wash fluid exceeds a level for which it is desired to flush at least a portion of the wash fluid from the tank and replace it with fresh water. If so, block 218 passes control to block 226 to perform a wash fluid refresh operation. In such an operation, one or both of dump valves 126 and 128 (or drain pumps, if used) may be actuated to drain at least a portion of the wash fluid in tank 102, and make up water valve 150 may be actuated to add make up water to the tank. In addition, during such an operation the filter may be cleaned concurrently with the flushing and refilling of wash fluid in some embodiments.

In one example embodiment, a wash fluid refresh operation may incorporate the following sequence of actions:
1. Position washing system in wash position
2. Open valve 126 (V1) and valve 152 (S2)
3. Wait 3 Sec
4. Open valve 128 (V2)
5. Wait 3 Sec
6. Open valve 154 (S3) and valve 150 (S1)
7. Wait 5 Sec
8. Close valve 126 (V1) and valve 152 (S2)
9. Wait 5 Sec
10. Close valve 154 (S3)
11. Wait 10 Sec
12. Close valve 128 (V2)
13. Fill until fluid level sensor 166 indicates full tank
14. Run pump 138 for 10 Sec
15. Wait 5 Sec
16. Recheck turbidity, and if turbidity is below threshold, return washing system to load position for next washing operation, otherwise repeat steps 1-16

It will be appreciated that other sequences may be used in other embodiments. Moreover, while in some embodiments a wash fluid refresh operation may replace all wash fluid with fresh water, in other embodiments only a portion of the wash fluid may be flushed and replaced with fresh water.

Returning to block 220, the block determines whether a need exists for a filter cleaning operation by determining if the pressure differential between pressure sensors 172, 174 meets a threshold, e.g., a pressure differential greater than some threshold that indicates that fluid flow through the filter has been impeded to an extent that cleaning of the filter is desirable. If so, block 220 passes control to block 228 to clean the filter, e.g., by actuating cleanout valve 152 and filter clean valve 154 to run fresh water over the outer surface of the filter element.

In one example embodiment, a filter cleaning operation may incorporate the following sequence of actions:
1. Open valve 152 (S2)
2. Wait 3 Sec
3. Open valve 154 (S3) for 5 seconds and then close
4. Wait 3 Sec
5. Close valve 152 (S2)
6. Check wash fluid level and fill as needed Returning to block 224, the block determines whether a need exists to add make up water to the tank by determining if the wash fluid level sensed by fluid level sensor 166 meets a threshold, e.g., is below a minimum fluid level. If so, block 224 passes control to block 230 to actuate make up water valve 150 to add makeup water, until the fluid level sensor indicates that the tank is full, whereby valve 150 may be shut off. In some embodiments, block 224 may be performed at the same time as blocks 218 and 220; however, it may be desirable to defer block 224 to allow for wash fluid in the wash chamber to have time to fully drain into the tank before checking the fluid level in the tank.

It will be appreciated that, assuming none of the supplemental operations of blocks 226, 228 and 230 are required, the bulk of the runtime of a washing operation is occupied by the washing, UV sanitizing and drying actions performed in blocks 206-212, and it will also be appreciated that the UV sanitizing action overlaps in time with each of the washing and drying actions, such that, for example, if the washing action takes X seconds and the drying action takes Y seconds, the UV sanitizing action takes Z=X+Y seconds. In other embodiments, particularly where a holder is moved between multiple stations, however, the UV sanitizing action may overlap only a portion of one or both of the washing and drying actions, or may not overlap with either of the washing and drying actions at all. In addition, it will be appreciated that moving between the loading, washing, and unloading positions may also occupy some time within a washing operation in some embodiments. It may be desirable in some embodiments, for example, to provide a washing operation having a duration of about 45 seconds or less, with, for example, about 5 seconds used to move from the loading position to the washing position, about 30 seconds for the washing action, about 5 seconds for the drying action, about 30 seconds for the UV sanitizing action (concurrent with the washing action, or alternatively in another embodiment about 35 seconds concurrently with both the washing and drying actions), and about 5 seconds to move from the washing position to the unloading position.

It will be appreciated that washing system 10 may vary in other embodiments in a number of manners. For example, an additional filter may be used in first chamber 104 of tank 102 in some embodiments to filter wash fluid before it is transferred to second chamber 106. Further, in some embodiments, a separate rinse action may be performed using a source of fresh water after the washing action. Further, in some embodiments, one or more disinfecting agents, e.g., various hypochlorite sanitizing compositions, may be introduced into tank 102 and maintained at a minimum level based upon sensing by a suitable sensor. In addition, further operations, such as startup operations that initialize the washing system, and shutdown operations that flush the washing system and shut down all components, may also be supported.

Concentric Housing Members

As noted above, while in some embodiments a holder may be movable between a plurality of stations during a washing operation, in other embodiments it may be desirable to utilize a holder that maintains the beverage container in a single location while various actions associated with a washing operation (e.g., loading, unloading, washing, rinsing, UV sanitization and/or drying) are performed. Furthermore, while in some embodiments a beverage container may be inserted into and removed from a beverage container washing system through a single opening, in other embodiments it may be desirable to utilize a housing configuration that enables a beverage container to be inserted into a washing system and removed from the washing system through separate openings, e.g., in a retail environment such that a customer may insert an unwashed beverage container into one side of a washing system built into or supported on a retail counter and an employee may remove the beverage container from the other side of the washing system after washing is complete, thereby minimizing employee contact with unwashed customer beverage containers.

To address these concerns, it may be desirable to utilize a washing system design that incorporates a pair of concentric housing members that are supported on a base, with an inner one of the concentric housing members being disposed inwardly from the outer one of the concentric housing members and forming at least a portion of a wash chamber, and with each of the concentric housing members including an opening. At least one of the concentric housing members may also be rotatable about an axis of rotation, e.g., under the control of a drive assembly, to selectively align the respective openings in the inner and outer concentric housing members to either enable or inhibit access to the wash chamber, e.g., to enable a user to insert or remove a beverage container into or from a holder disposed in the wash chamber when the openings are aligned, or to restrict external access to the holder in the wash chamber during the washing operation, and in some instances, prevent any wash fluid sprayed in the wash chamber during the washing operation from escaping from the washing system.

In some instances, the axis of rotation may be vertical, and moreover, in some instances, multiple openings may be provided in either or both of the inner and outer concentric housing members to provide different points of access to the wash chamber (e.g., to provide separate openings for a customer and an employee, or otherwise provide separate openings on different sides of a washing system). Further, while in some embodiments, only a single concentric housing member may be rotatable, with the other concentric housing member remaining fixed or stationary, in other embodiments, both concentric housing members may be rotatable.

Beverage container washing system 10 of FIGS. 1-2 illustrates such a concentric housing member arrangement, where concentric housing member 62 and outer concentric housing member 64 are configured as concentric domes that are generally dome shaped and have generally cylindrical sidewalls. It will be appreciated, however, that the concentric housing members can have a wide variety of alternate shapes, sizes and configurations, so the invention is not limited to the concentric dome configuration illustrated herein. As one example, in one embodiment an inner concentric housing member may have an open-top, e.g., configured as a cylinder, such that the top of the wash chamber is defined at least in part by the outer concentric housing member. By doing so, drying, spraying and/or ultraviolet sanitization actions may be performed at least in part by stationary components operating from an overhead position and not requiring electrical or other connections to a movable concentric housing member.

Figure 7:
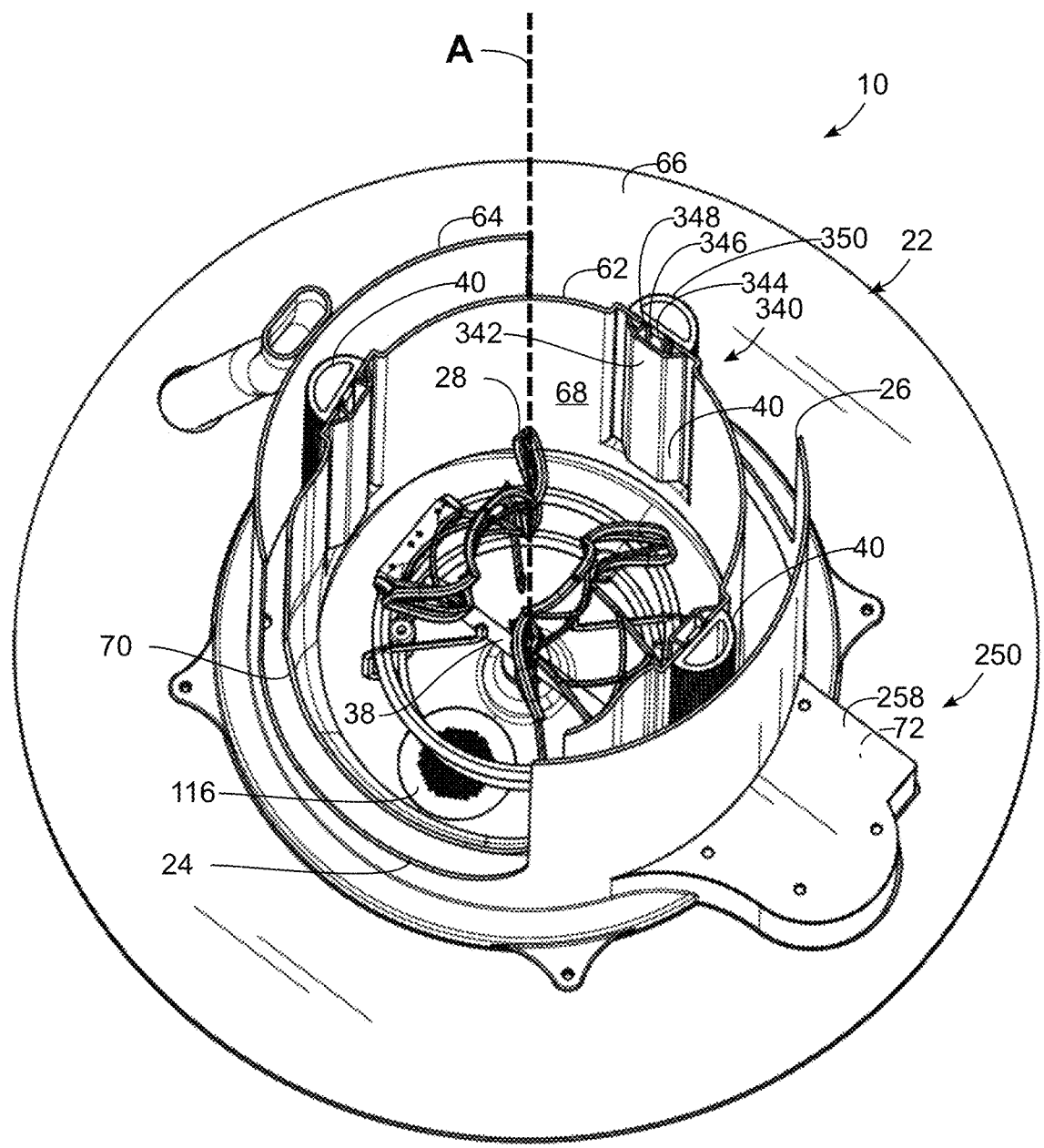
FIGS. 7-9 are cross-sectional views taken through the countertop portion of the beverage container washing system of FIG. 1 in respective loading, washing and unloading configurations.
Figure 8:
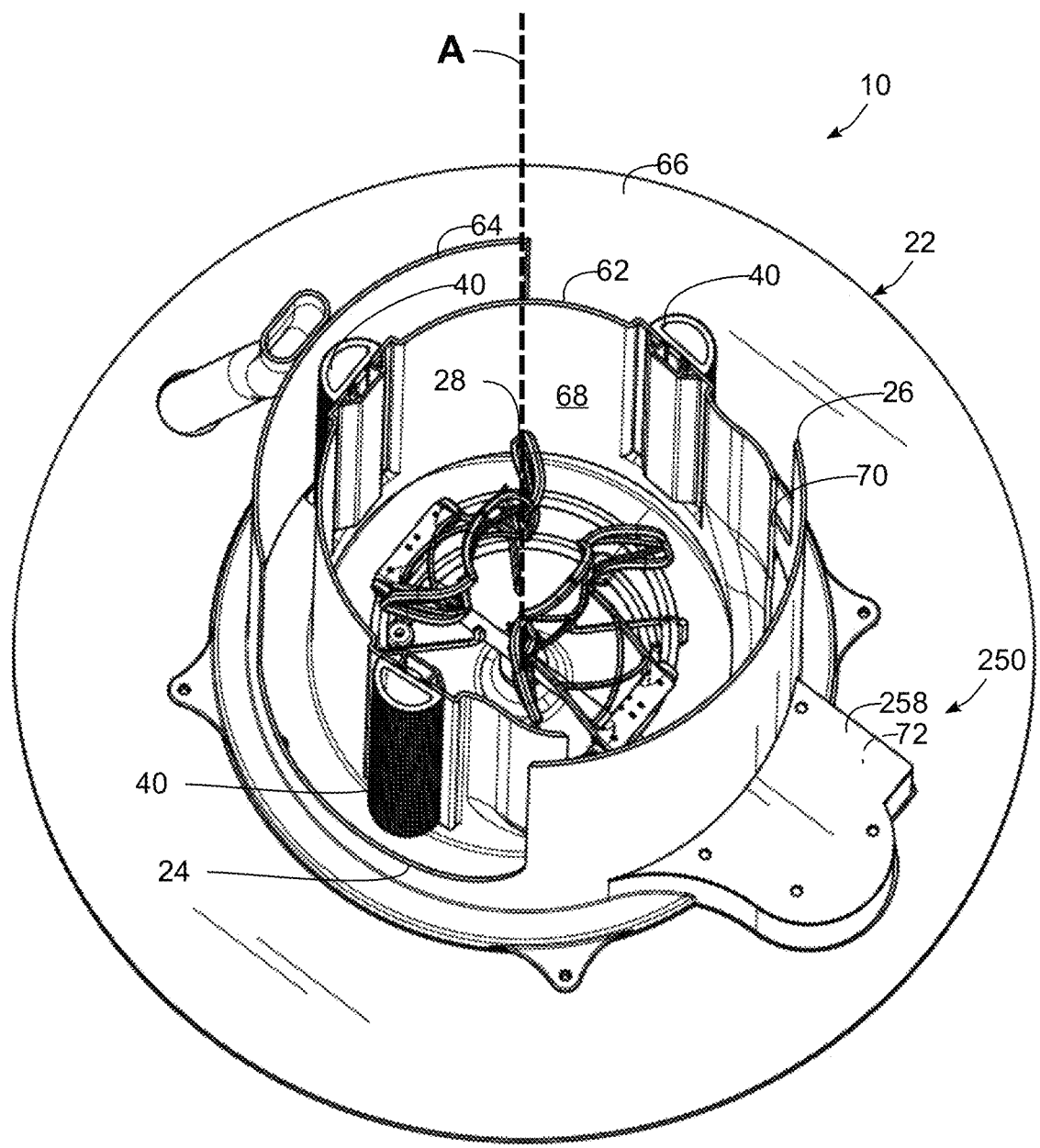
Figure 9:
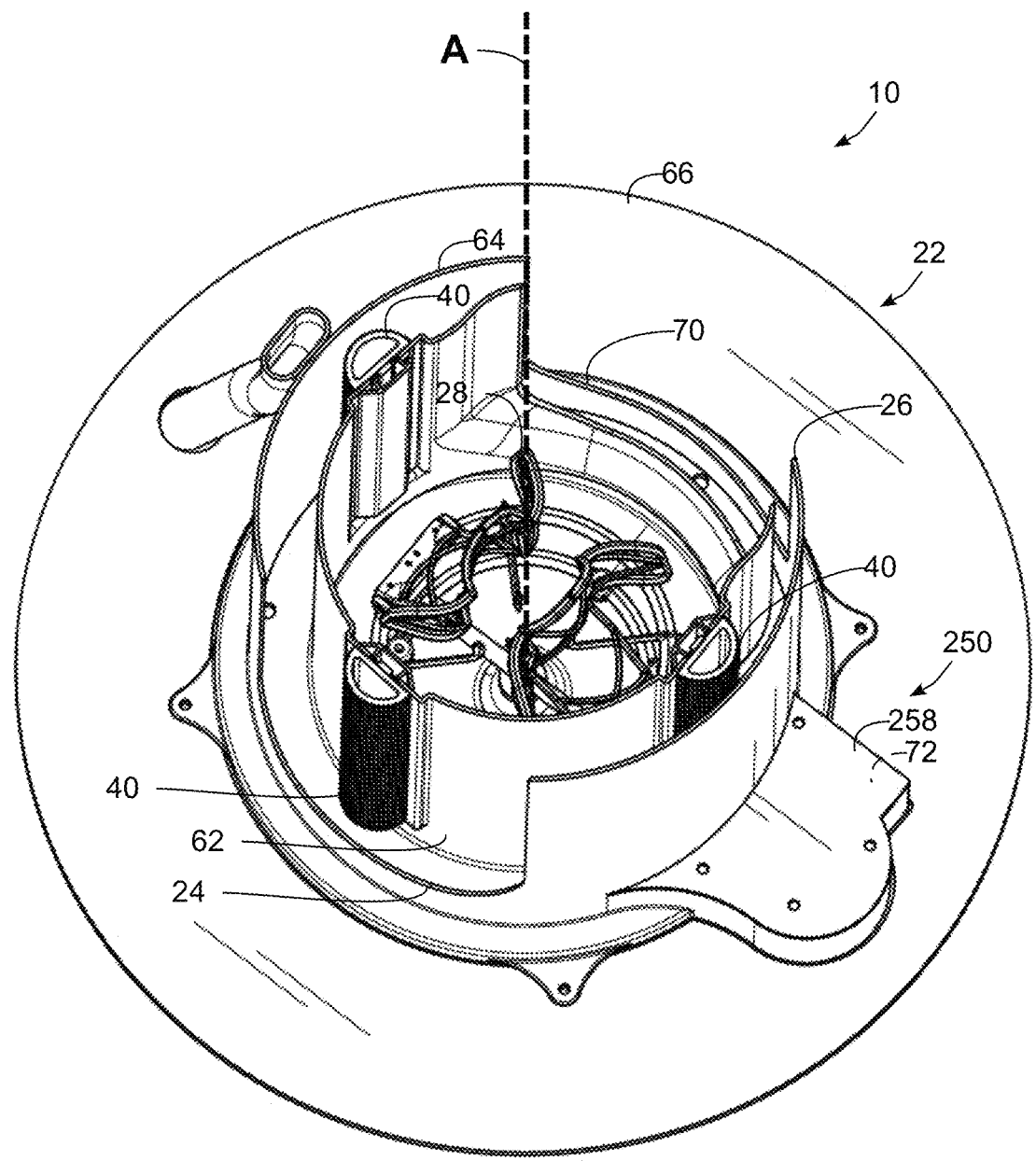

With further reference to FIGS. 7-9, each concentric housing member 62, 64 fully circumscribes an axis of rotation A, and among the concentric housing members 62, 64, inner concentric housing member 62 is rotatable while outer concentric housing member 64 is fixed or stationary. An entrance opening 24 and exit opening 26 are defined on opposite sides of outer concentric housing member 62 while an additional opening 70 is provided in inner concentric housing member 64, and a drive motor 72 is used to rotate inner concentric housing member 64 to selectively move opening 70 between a loading position where opening 70 is aligned with entrance opening 24 to provide access to the wash chamber for insertion of the beverage container prior to a washing operation (FIG. 7), a washing position where opening 70 is intermediate entrance and exit openings 24, 26 (thereby effectively closing both openings as shown in FIG. 8), and an unloading position where opening 70 is aligned with exit opening 26 to provide access to the wash chamber for removal of the beverage container at the completion of a washing operation (FIG. 9). The loading, washing and unloading positions represent different relative positions between the two concentric housing members 62, 64.

It will be appreciated that in some embodiments, the mere alignment or misalignment of opening 70 and entrance and exit openings 24, 26 may be sufficient to inhibit the escape of wash fluid from wash chamber 68. It should also be noted that opening 70 as illustrated in the figures does project radially from the inner cylindrical wall defining the wash chamber such that an edge of opening 70 may touch or at least define a reduced gap between opening 70 and the inner cylindrical wall of outer concentric housing member 64. In other embodiments, however, it may be desirable to also include a sealing arrangement on one or both of concentric housing members 62, 64 (e.g., around one or more of openings 24, 26 and 70) to further inhibit the escape of wash fluid from wash chamber 68.

Figure 10:
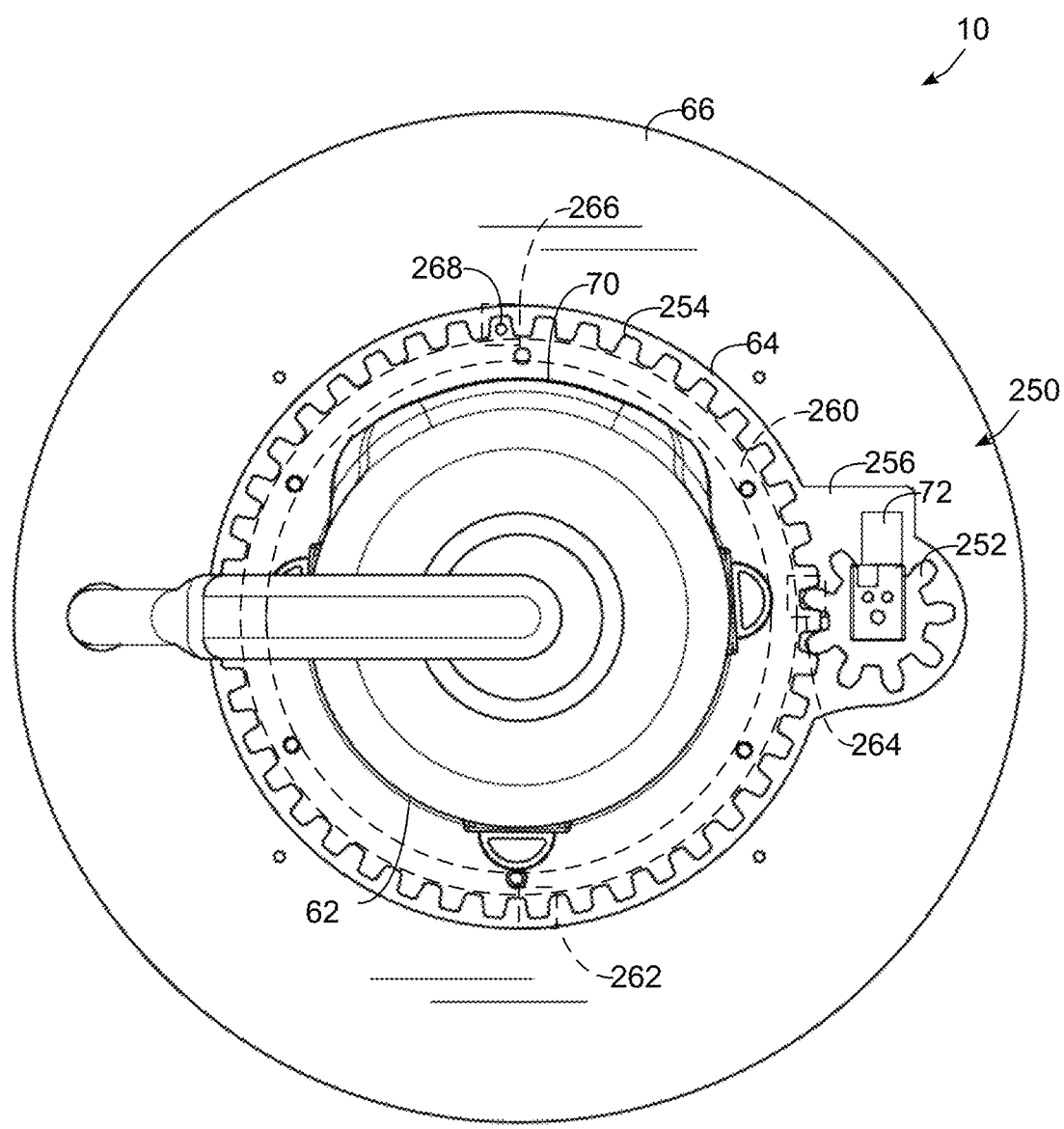
FIG. 10 is a partial top plan view of the beverage container washing system of FIG. 1, with portions thereof removed to illustrate a housing drive system thereof.

With additional reference to FIG. 10, drive motor 72 may be incorporated into a drive assembly 250 that further includes a pair of gears 252, 254 configured to drive rotation of inner concentric housing member 62 with drive motor 72. Drive motor 72 may be an electric, e.g. a DC motor, and drive motor 72 and gear 252 may be disposed in a compartment 256 formed in outer concentric housing member 64, and may be accessed through a cover 258. Gear 254 may be coupled to inner concentric housing member 62, and in some embodiments, may circumscribe the perimeter of the inner concentric housing member. In some embodiments, gear 254 may also be formed integrally with inner concentric housing member 62. In another embodiment, gear 254 may be formed as an internal ring gear and may be driven from a point inward from inner concentric housing member 62. Inner concentric housing member 62 may be rotatably supported on a turntable bearing 260. In other embodiments, other drive assembly configurations may be used to drive rotation of inner concentric housing member 62, e.g., a friction wheel drive assembly, a belt or chain drive, a piston or linear motor drive, etc. Particularly where rotation is limited to only about 90 degrees, as may be the case when two openings are provided in inner concentric housing member 62, various mechanical arrangements, including linear drives, may be used to impart sufficient rotation to the inner concentric housing member.

Furthermore, in order to controllably rotate inner concentric housing member 62 between the different relative positions, a position detector, e.g., an encoder or other suitable position sensor, may be used. In one embodiment, for example, a position detector may be implemented by a set of stationary three reed switches 262, 264, 266 configured to sense a magnet 268 coupled to inner concentric housing member 62 when the opening 70 is in each of the loading, washing and unloading positions. Other position detector configurations may be used in other embodiments, however, so it will be appreciated that the invention is not limited to the particular configuration illustrated in FIG. 10.

Dryer Assembly

As noted above in connection with FIGS. 1-2, it may also be desirable in some embodiments to incorporate a dryer assembly in a beverage container washing system, e.g., to blow off any standing wash fluid, water or other moisture left on the beverage container subsequent to spraying by a spraying assembly. It will be appreciated, however, that where the housing of the beverage container washing system incorporates movable components, supplying a flow air to the beverage container can be complicated by the need to supply the air in a manner that accommodates the movable components.

In the specific case of beverage container washing system 10, which incorporates a rotatable inner concentric housing member 62, for example, it is generally desirable to provide a flow of air to wash chamber 68, but do so in a manner that accommodates the rotatable nature of inner concentric housing member 62.

Figure 11:
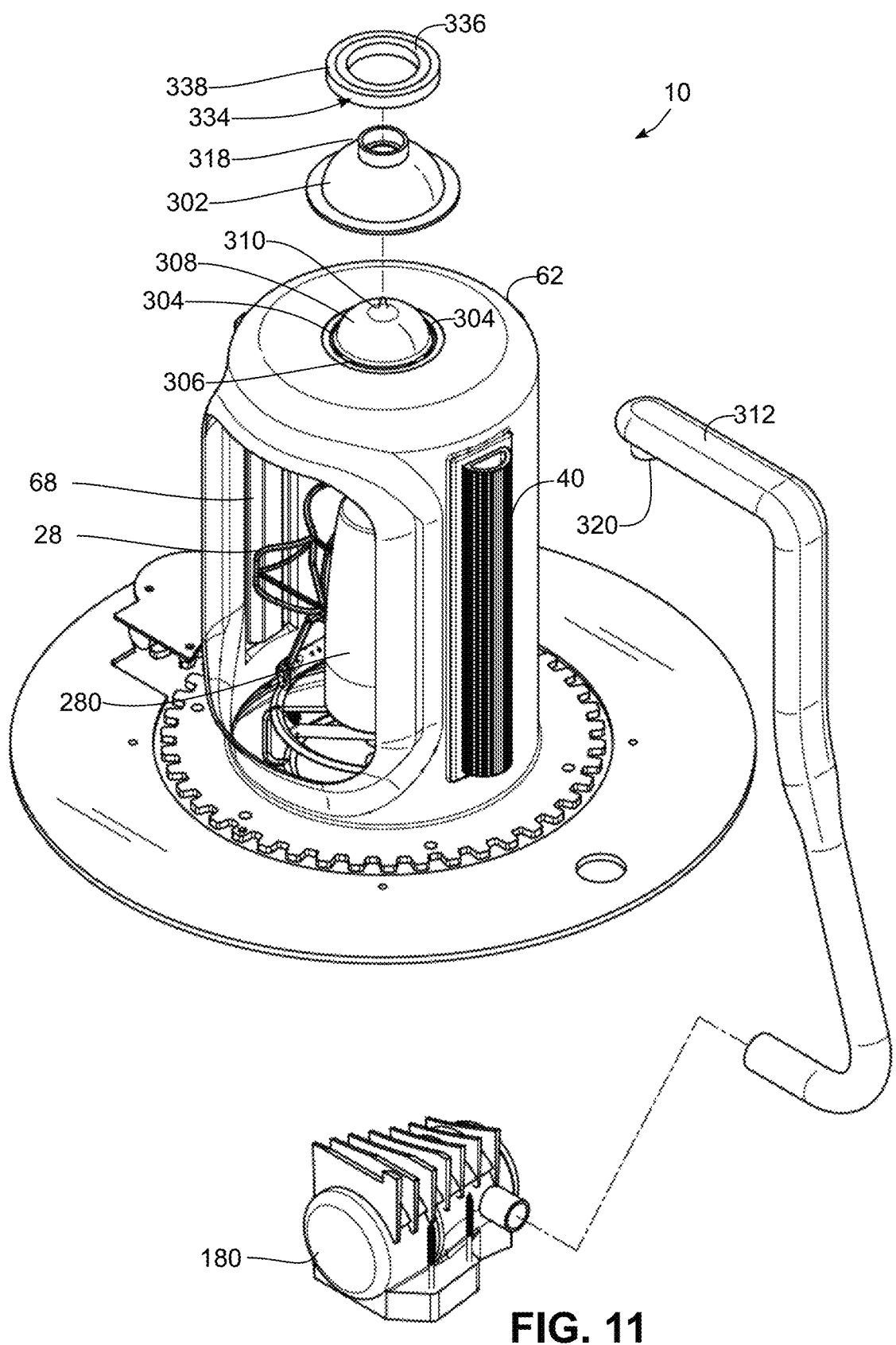
FIG. 11 is an exploded top perspective view of dryer assembly and ultraviolet sanitizing assembly components of the beverage container washing system of FIG. 1.
Figure 12:
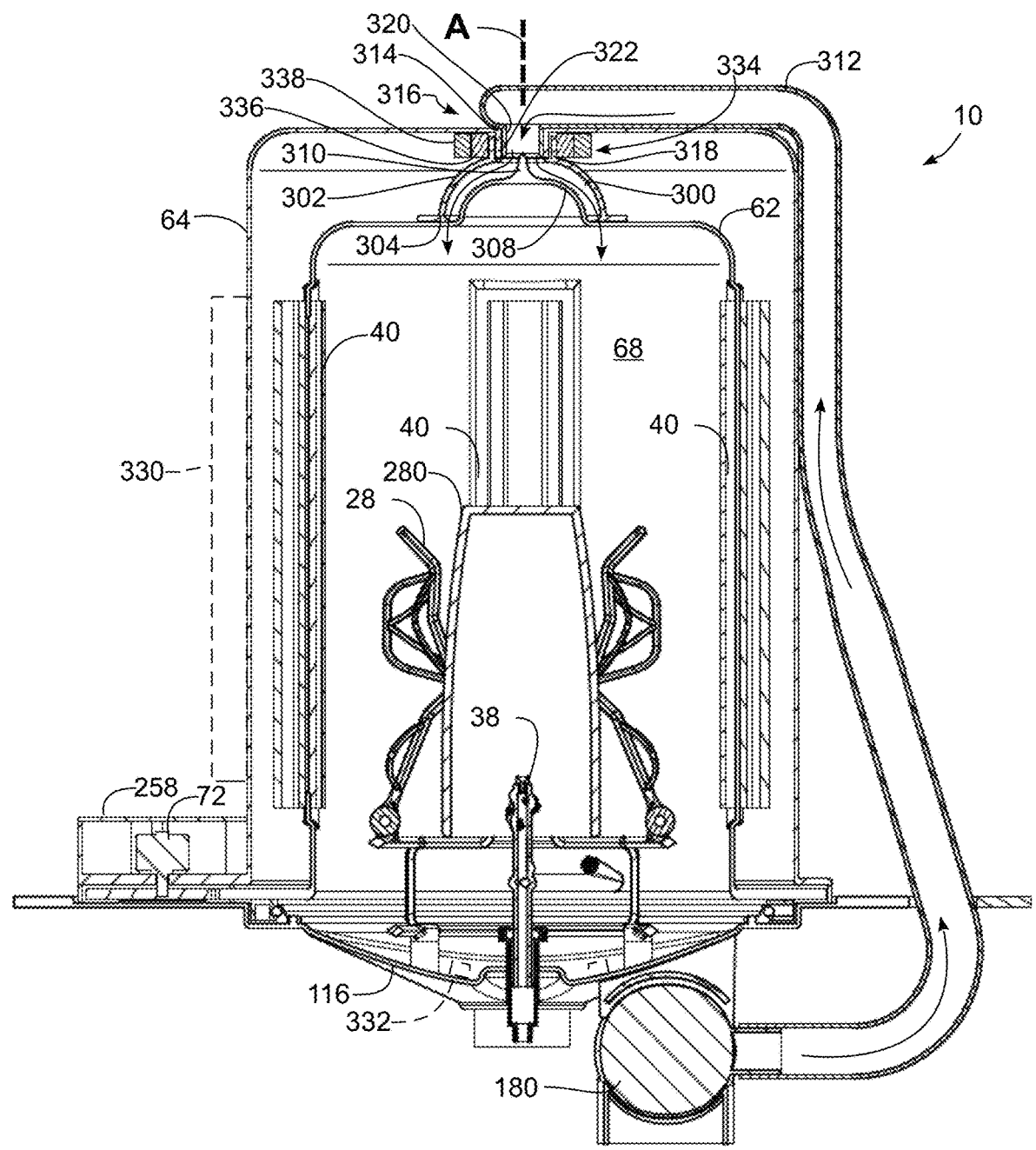
FIG. 12 is a side cross-sectional view of dryer assembly and ultraviolet sanitizing assembly components of the beverage container washing system of FIG. 1.

In the illustrated embodiment, and with further reference to FIGS. 11-12 (note that outer concentric housing member 64 has been omitted from FIG. 11), a dryer assembly may include an air knife chamber 300 disposed proximate a top of inner concentric housing member 62. Air knife chamber 300 is defined in part by an outer shell 302, which, in some embodiments, may be integrally molded or formed with inner concentric housing member 62, while in other embodiments, may be welded, fastened, or otherwise secured to a wall of inner concentric housing member 62 such that the outer shell 302 covers at least a portion of the wall of the inner concentric housing member. In the illustrated embodiment, outer shell 302 and air knife chamber 300 are configured to rotate with the inner concentric housing member, while in other embodiments, outer shell 302 and air knife chamber 300 may be stationary, such that inner concentric housing member 62 rotates relative to the outer shell and the air knife chamber.

One or more air knife openings 304 are defined in inner concentric housing member and are in fluid communication with air knife chamber 300 to direct a flow of air toward a beverage container 280 while the beverage container is held by holder 28 in wash chamber 68. In the illustrated embodiment, for example, an annular arrangement of four radially-offset and arcuate air knife openings 304 (which at least partially circumscribe the axis of rotation A) are used, which are separated from one another by four tabs 306 that support a central hub 308 having a central nipple 310. As seen in FIG. 12, the shape of central hub 308 and central nipple 310 serves to distribute air flow radially outwardly to the air knife openings 304 that are radially-offset from the axis of rotation A. Moreover, in the illustrated embodiment, central nipple is upwardly-facing and axially aligned with the axis of rotation A.

Air is suppled to air knife chamber 300 from a stationary air supply conduit 312 that is in fluid communication with blower 180 to receive a supply of pressurized air. In the illustrated embodiment, at least a portion of conduit 312 extends substantially vertically along a side of outer concentric housing member 64, around a top side of outer concentric housing member 64, and then through an opening 314 formed in the top side of outer concentric housing member 64.

Air knife chamber 300 is in fluid communication with stationary air supply conduit 312 through a rotary seal 316, which in the illustrated embodiment is formed by a three concentric tubes 318, 320, 322 that are all axially aligned with the axis of rotation A. Concentric tube 318 is an upwardly-facing tube that defines an air inlet for air knife chamber 300, while concentric tube 320 is a downwardly-facing tube that extends downwardly from stationary air supply conduit 312 and forms an air outlet therefor. Concentric tube 322 is also downwardly-facing, but extends downwardly from outer concentric housing member 64 and defines opening 314. In the illustrated embodiment, concentric tube 322 is inward of concentric tube 318, and concentric tube 320 is inward of concentric tube 322, with at least portions of all three concentric tubes overlapping with one another to form the rotary seal. Moreover, in some embodiments, rotary seal 316 also functions as an axle for rotation of inner concentric housing member 62 to rotate about axis of rotation A. As such, air from stationary air supply conduit 312 may be provided to wash chamber 68 through rotating concentric housing member 62.

It will be appreciated that other rotary seals may be used in other embodiments, so the invention is not limited to the concentric tube arrangement illustrated in FIGS. 11-12. Moreover, it will be appreciated that a wide variety of alternate numbers and configurations of air knife openings may be used in other embodiments, e.g., to direct air in multiple directions and at other regions of a beverage container, including, in some embodiments, an interior of the beverage container. Additional stationary air knife openings may also be used in some embodiments, e.g., directed upwardly from base 66, and in some embodiments, no movable air knives may be used, or drying may not be supported whatsoever in a cup washing system. Where an inner concentric housing member has an open top, as another example, stationary air knives may be used in lieu of the configuration illustrated in FIGS. 11-12. Further, air knife openings may be configured in other manners in other embodiments, e.g., using nozzles capable of controlling direction, flow rate and/or spray pattern, as will be appreciated by those of ordinary skill in the art having the benefit of the instant disclosure.

Ultraviolet Sanitizing Assembly

As also noted above in connection with FIGS. 1-2, it may also be desirable in some embodiments to incorporate an ultraviolet sanitizing assembly in a beverage container washing system, e.g., to sanitize an outer and/or inner surface of a beverage container by irradiating it with ultraviolet light. It will be appreciated, however, that where the housing of the beverage container washing system incorporates movable components, supplying power to ultraviolet lights mounted to such movable components can be complicated by the need to supply the power in a manner that accommodates the movable components. In the specific case of beverage container washing system 10, which incorporates a rotatable inner concentric housing member 62, for example, it may be desirable to provide one or more ultraviolet lights 40 within wash chamber 68, but do so in a manner that accommodates the rotatable nature of inner concentric housing member 62.

Ultraviolet sanitizing lights, which are generally formed by arrays of ultraviolet (UV) light emitting diodes (LEDs), or alternatively by other devices capable of emitting ultraviolet light (e.g., incandescent or halogen lights), are susceptible to being attenuated by materials lacking sufficient transmissivity to ultraviolet wavelengths, and in some instances, UV LEDs may require special materials that offer a unique transmissivity, as the UV light may be attenuated even by some visually translucent materials. As such, it may be desirable in some embodiments to avoid the high cost of creating large parts that are UV light transmissive by restricting the amount of material between the UV LEDs and the beverage container to be sanitized. In the illustrated embodiment, therefore, incorporating UV LEDs into the inner concentric housing member 62 may reduce potential transmissivity issues, and may even allow for the inner concentric housing member 62 to be formed from a material that is translucent or transparent to visible light but that is more opaque to ultraviolet light. Various materials that may be used in some embodiments are polycarbonate, acrylic, standard Glass, etc., although other materials may be used. In some instances, this may even provide a pleasing visual effect for users, as the visual light emitted by the UV LEDs may be visible through the inner (and outer, if formed of a similar material) concentric housing member 62, while still blocking user exposure to ultraviolet wavelengths.

In the illustrated embodiment, and with continuing reference to FIGS. 11-12 (note that outer concentric housing member 64 has been omitted from FIG. 11), an ultraviolet sanitizing assembly may include one or more ultraviolet lights 40 that are coupled to a rotatable concentric housing member, in this case inner concentric housing member 62. As noted above, while ultraviolet lights 40 may be implemented using one or more UV LEDs, in other embodiments, other devices capable of emitting ultraviolet light (e.g., incandescent or halogen lights) may also be used. In other embodiments, e.g., where an outer concentric housing member is rotatable, one or more ultraviolet lights may be mounted to an outer concentric housing member. Further, in some embodiments, additional ultraviolet lights may be located in fixed or stationary locations, e.g., as illustrated in FIG. 12 by ultraviolet light 330 on outer concentric housing member 64, as illustrated in FIG. 12 by ultraviolet light 332 in collector 116, or in other locations such as the space between concentric housing members 62, 64.

It should be noted that in some embodiments ultraviolet light 330 may be positioned on outer concentric housing member 64 such that opening 70 of inner concentric housing member 62 faces ultraviolet light 330 when in the washing position, such that three ultraviolet lights 40 may be disposed on inner concentric housing member 62, and with all four ultraviolet lights 40, 330 evenly spaced in 90 degree increments about the axis of rotation to provide relatively full coverage of the outer surface of beverage container 280. It should also be noted that some ultraviolet lights, e.g., ultraviolet light 332, may be positioned to irradiate an inner surface of beverage container 280.

In order to power ultraviolet lights 40, a slip ring 334 may be coupled between inner and outer concentric housing members 62, 64, with, for example, a rotatable portion 336 coupled to inner concentric housing member 62 and a stationary portion coupled to outer concentric housing member 64. Slip ring 334 may utilize various electromechanical constructions, including rotary electrical contacts, commutators, rotary transformers, rotary unions, pancake slip rings, wireless slip rings, etc., and wiring harnesses (not shown) both on the stationary and rotatable sides of the slip ring may be used to route the electrical power to each ultraviolet light 40. Further, slip ring 334 may be positioned elsewhere within housing 22, e.g., along the top or side wall of inner concentric housing member 62, at the base of inner concentric housing member 62, etc.

Various ultraviolet light constructions may be used for ultraviolet lights 40 in different embodiments. In the illustrated embodiment, for example, each ultraviolet light 40 may extend substantially vertically along a side wall of inner concentric housing member 62, and in some instances, and as best illustrated in FIGS. 7-9, the inner concentric housing member 62 may include a substantially vertical mounting arrangement 340 configured to receive each ultraviolet light 40.

The mounting arrangement 340 in some embodiments may include an ultraviolet transmissive cover 342 that overlays ultraviolet light 40 to permit ultraviolet light transmission into wash chamber 68, and that further seals the ultraviolet light from the wash chamber. In some instances, the cover 342 may be mounted, welded or otherwise secured to inner concentric housing member 62, while in other instances, the cover may be integrally molded thereto. In either instance, it is generally desirable for the other walls of inner concentric housing member 62 to be formed of an ultraviolet blocking material that inhibits ultraviolet light transmission through the walls of inner concentric housing member 62.

The mounting arrangement may 340 may also include one or more openings 344 formed in a wall of inner concentric housing member 62 and aligned with a plurality of UV LEDs 346 disposed on a circuit board 348. By doing so, circuit board 348 may be positioned on an outer surface of inner concentric housing member 62, with the UV LEDs 346 positioned to emit ultraviolet light through openings 344. In addition, in some embodiments, it may also be desirable to incorporate a heat sink 350, which may run along a portion or the entire length of circuit board 348 and be thermally coupled thereto, and serve to further seal the circuit board from the surrounding environment.

It will be appreciated that different numbers and/or orientations of ultraviolet lights may be used in other embodiments, e.g., two ultraviolet lights having respective angular positions about the axis of rotation A spaced about 90 to about 180 degrees, or less, from one another, three ultraviolet lights having respective angular positions about the axis of rotation A spaced about 90 to about 120 degrees from one another, four ultraviolet lights having respective angular positions about the axis of rotation A spaced about 90 degrees or less from one another, etc. In one example embodiment, for example, two opposing ultraviolet lights may be supported on inner concentric housing member 62 and two opposing ultraviolet lights may be supported on outer concentric housing member 64 such that ultraviolet lights are oriented in 90 degree increments when the inner concentric housing member 62 is in the washing position.

Holder

Figure 13:
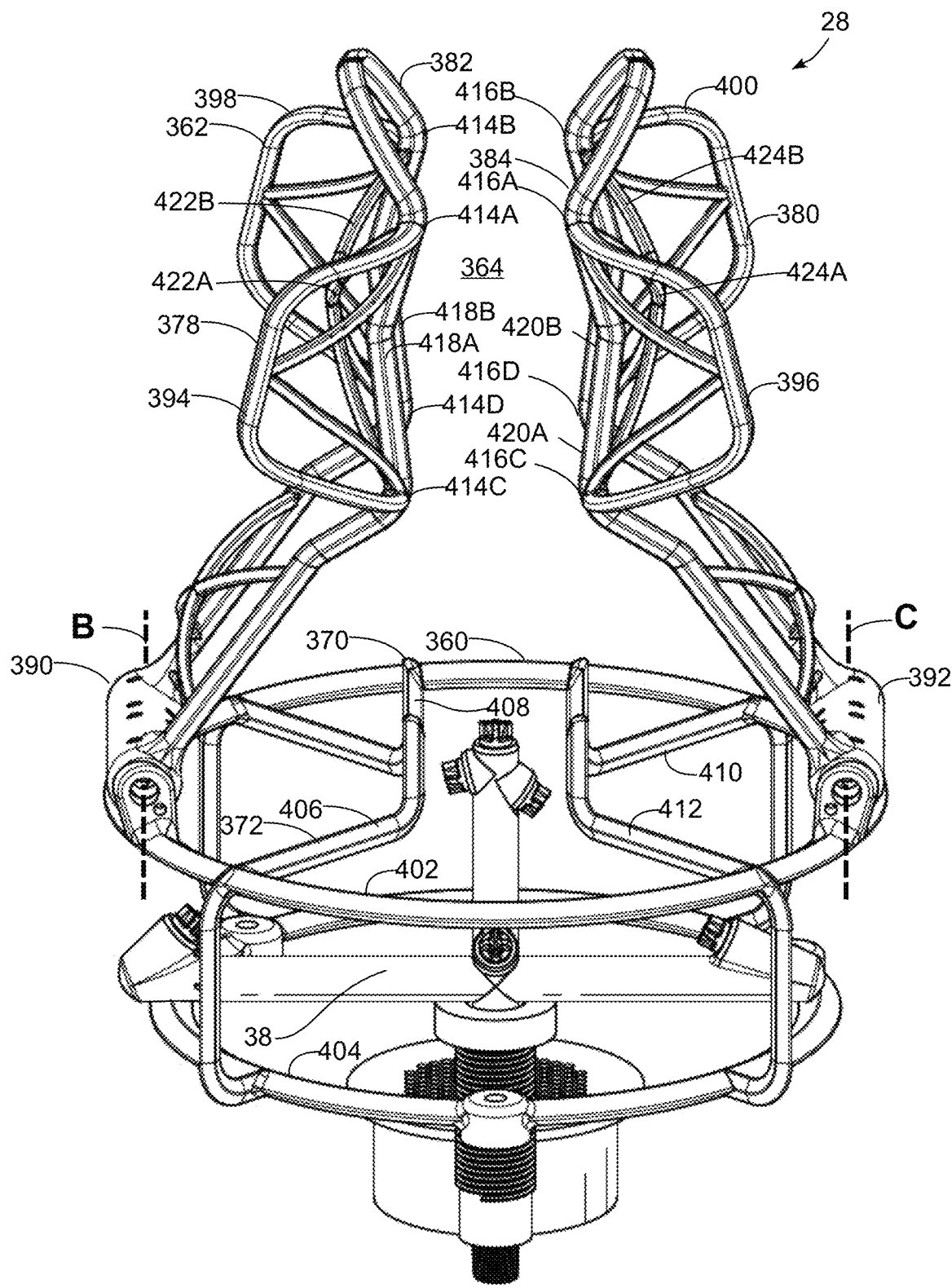
FIG. 13 is a side perspective view of example implementations of the holder and sprayer of the beverage container washing system of FIG. 1.

Now turning to FIG. 13, one example implementation of holder 28 is illustrated in greater detail. Holder 28 is configured to be positioned within wash chamber 68 and to hold a beverage container in an inverted orientation during a washing or sanitizing operation. In the illustrated embodiment, holder 28 includes a base 360 that is configured to support a beverage container when the beverage container is held by the holder in the inverted orientation, and a retainer 362 configured to support a sidewall of the beverage container when the beverage container is held by the holder in the inverted orientation. Retainer 362 in particular restricts lateral movement of the beverage container during the washing or sanitizing operation, and includes a lateral opening 364 through which the beverage container may be passed during insertion into and/or removal from the holder. The design of retainer 362 as illustrated in FIG. 13, in particular, attempts to provide minimal surface contact with washed beverage containers to maximize exposure to wash fluid and/or ultraviolet radiation. In some embodiments, a beverage container may even be allowed to rotate or otherwise "wiggle" around somewhat while being held by the retainer as a result of being sprayed such that the areas of the beverage container that are contacted by the retainer may change from time to time during a washing operation.

Figure 14:
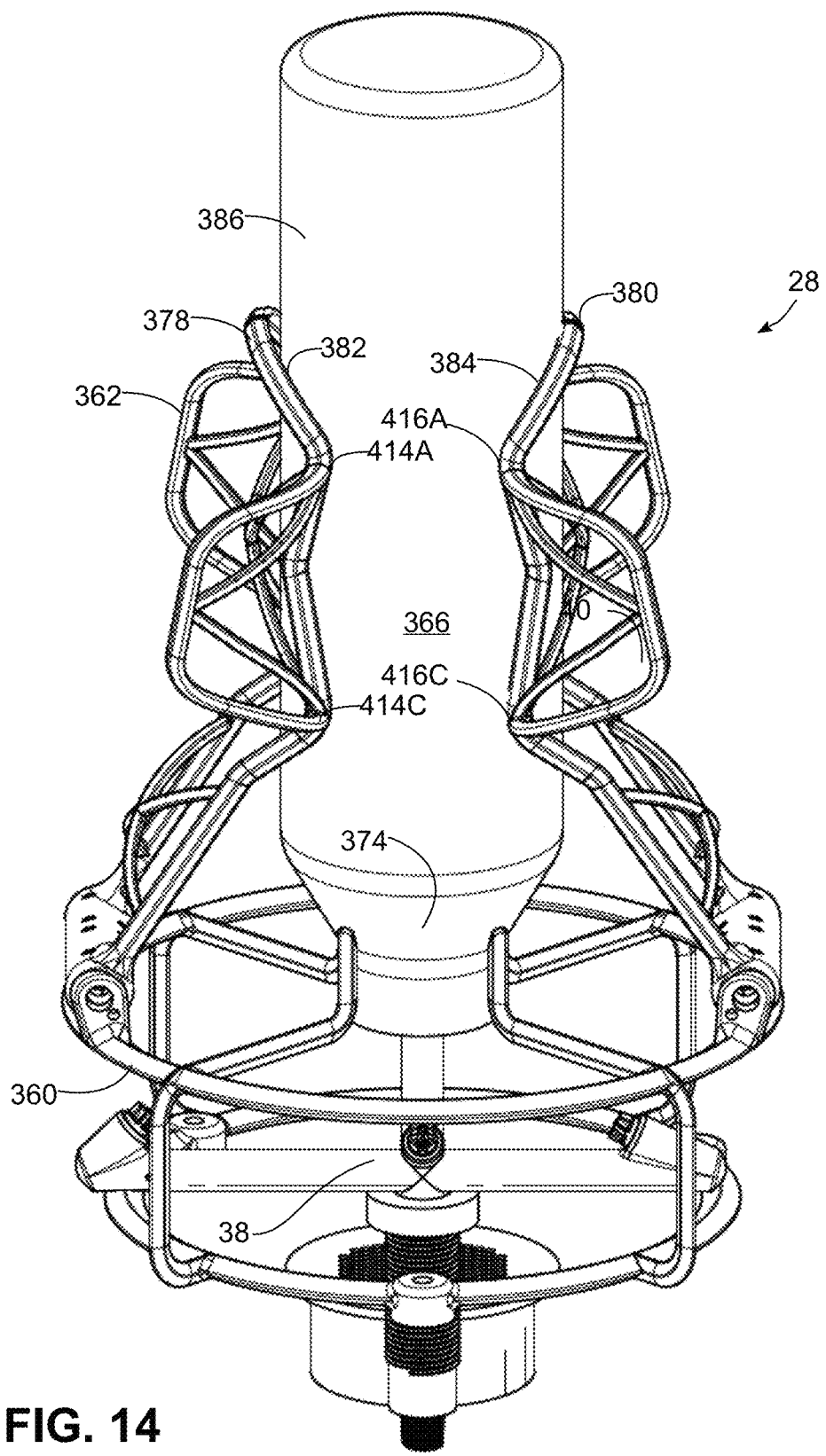
FIG. 14 is a side perspective view of the holder and sprayer of FIG. 13, with a narrow mouth beverage container held by the holder.
Figure 15:
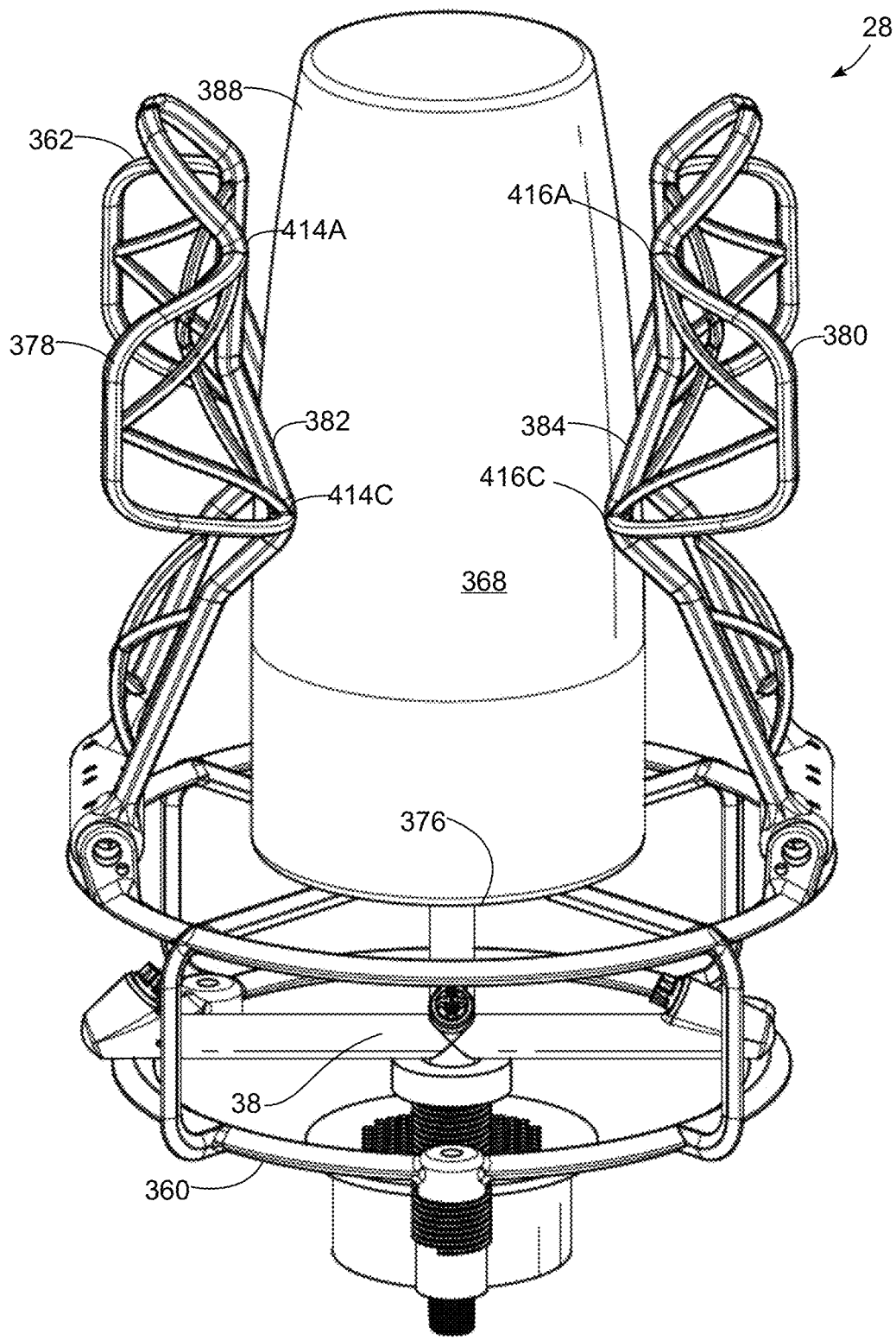
FIG. 15 is a side perspective view of the holder and sprayer of FIG. 13, with a wide mouth beverage container held by the holder.

Base 360 is desirably adapted to support beverage containers having various diameter mouths or openings. FIG. 14, for example, illustrates a narrow mouth beverage container 366 held by holder 28 and supported by base 360, while FIG. 15 illustrates a wide mouth beverage container 368 held by holder 28 and supported by base 360.

In the illustrated embodiment, for example, base 360 includes a substantially vertical portion 370 that projects upwardly towards the beverage container when the beverage container is held by the holder in the inverted orientation, and that defines a first annular support that may be used to support beverage containers having mouths or openings that are smaller than a predetermined amount, such that a narrow mouth beverage container such as beverage container 366 of FIG. 14 is supported on a shoulder 374 thereof. Base 360 also includes a substantially horizontal portion 372 that is disposed radially outwardly from the substantially vertical portion 370, and that defines a second annular support that may be used to support beverage containers having mouths or openings that are larger than a predetermined amount, such that a wide mouth beverage container such as beverage container 368 of FIG. 15 is supported on a lip 376 thereof. It should be appreciated also that, when a narrow mouth beverage container such as beverage container 366 of FIG. 14 is supported by base 360, substantially vertical portion 370 extends externally to the beverage container, but when a wide mouth beverage container such as beverage container 368 of FIG. 15 is supported by base 360, substantially vertical portion 370 extends internally to the beverage container. In both configurations, however, in the illustrated embodiment it will be appreciated that the lip or shoulder of a beverage container generally contacts the base at four points, arranged in a rectangular or diamond arrangement, which minimizes the amount of the lip that is blocked from spray and/or ultraviolet irradiation at any point in time.

Also, in the illustrated embodiment, retainer 362 includes a pair of opposing grippers 378, 380. Each gripper 378, 380 includes a container engaging portion 382, 384 that is configured to engage the sidewall of the beverage container (e.g., sidewalls 386, 388 of beverage containers 366, 368 of FIGS. 14 and 15), and each is movable between respective first and second positions, where in the first positions the container engaging portions 382, 384 are closer to one another than when in the second positions, and the lateral opening 364 is thus narrower when the container engaging portions 382, 384 are in the first positions than when in the second positions. FIG. 13, for example, illustrates grippers 378, 380 in their first positions and FIGS. 14 and 15 illustrate grippers 378, 380 in positions generally corresponding to the second positions, and it should be noted that movement of a gripper from its first position to its second position generally increases the lateral separation between the container engaging portions 382, 384 of grippers 378, 380.

Each gripper 378, 380 is supported on holder 28 through a hinge 390, 392, each of which pivots about a respective pivot axis B, C such that each of grippers 378, 380 moves between its respective first and second positions at least partially through rotation about the respective pivot axis B, C of hinge 390, 392. Moreover, in the illustrated embodiment, each hinge 390 is a spring-loaded hinge that biases each gripper 378, 380 to its first position as shown in FIG. 13. While the invention is not so limited, each hinge 390, 392 is supported by base 360 and pivot axes B, C are substantially horizontally oriented and substantially parallel to one another. It will be appreciated that other mechanisms for biasing each gripper may be used in other embodiments, and that other manners of supporting each gripper for movement between different positions (e.g., incorporating some degree of linear movement) may be used in other embodiments.

Each gripper 378, 380 also includes a pair of wing portions 394, 396, 398, 400 that are used to facilitate insertion of a beverage container into the holder. Wing portions 394, 398 are disposed on a first side of lateral opening 364 and wing portions 396, 400 are disposed on a second, opposite side of lateral opening 364, and each wing portion 394-400 is inclined relative to an insertion direction such that when the beverage container is pushed into the lateral opening and against the wing portions (wing portions 394, 398 on one side of lateral opening 364, and wing portions 396, 400 on the other side of lateral opening 364), grippers 378, 380 are urged toward their respective second positions.

Holder 360 may be formed using various materials, and is desirably formed of materials that are water and rust resistant. Further, holder 360 desirably has a construction that minimizes the amount of surface area of the beverage container that is blocked from ultraviolet radiation and/or spray of wash fluid while the beverage container is held by the holder. In the illustrated embodiment, for example, holder 360 is predominantly formed of a wire frame, e.g., a cast metal or welded stainless steel wire frame including a truss-like support structure.

Base 360, for example, may include a pair of rings 402, 404 defining a perimeter of the base and supporting a plurality of (e.g., four) wires 406, 408, 410, 412 that effectively define the substantially vertical portion 370 and substantially horizontal portion 372 of base 360 through corresponding horizontal and vertical portions of each wire, e.g., as shown in FIG. 13. Each wire 406-412 may also include an inclined end in some embodiments to adapt to the shoulder of a narrow mount beverage container.

Also, in the illustrated embodiment, each container engaging portion 382, 384 includes a set of four contact points 414A-D, 416A-D disposed in a substantially rectangular or diamond arrangement. Moreover, due to the pivoting nature of grippers 378, 380, depending upon the diameter of the beverage container held by the holder, all eight contact points 414A-D, 416A-D may contact the sidewall of the beverage container, or only a subset of four of contact points 414A-D, 416A-D may contact the sidewall of the beverage container. Beverage container 366 of FIG. 14, for example, has a smaller diameter, and as a result is contacted only by the upper contact points 414A, 414B, 416A and 416B, while beverage container 368 of FIG. 15 has a larger diameter, and as a result is contacted only by the lower contact points 414C, 414D, 416C and 416D.

Figure 16:
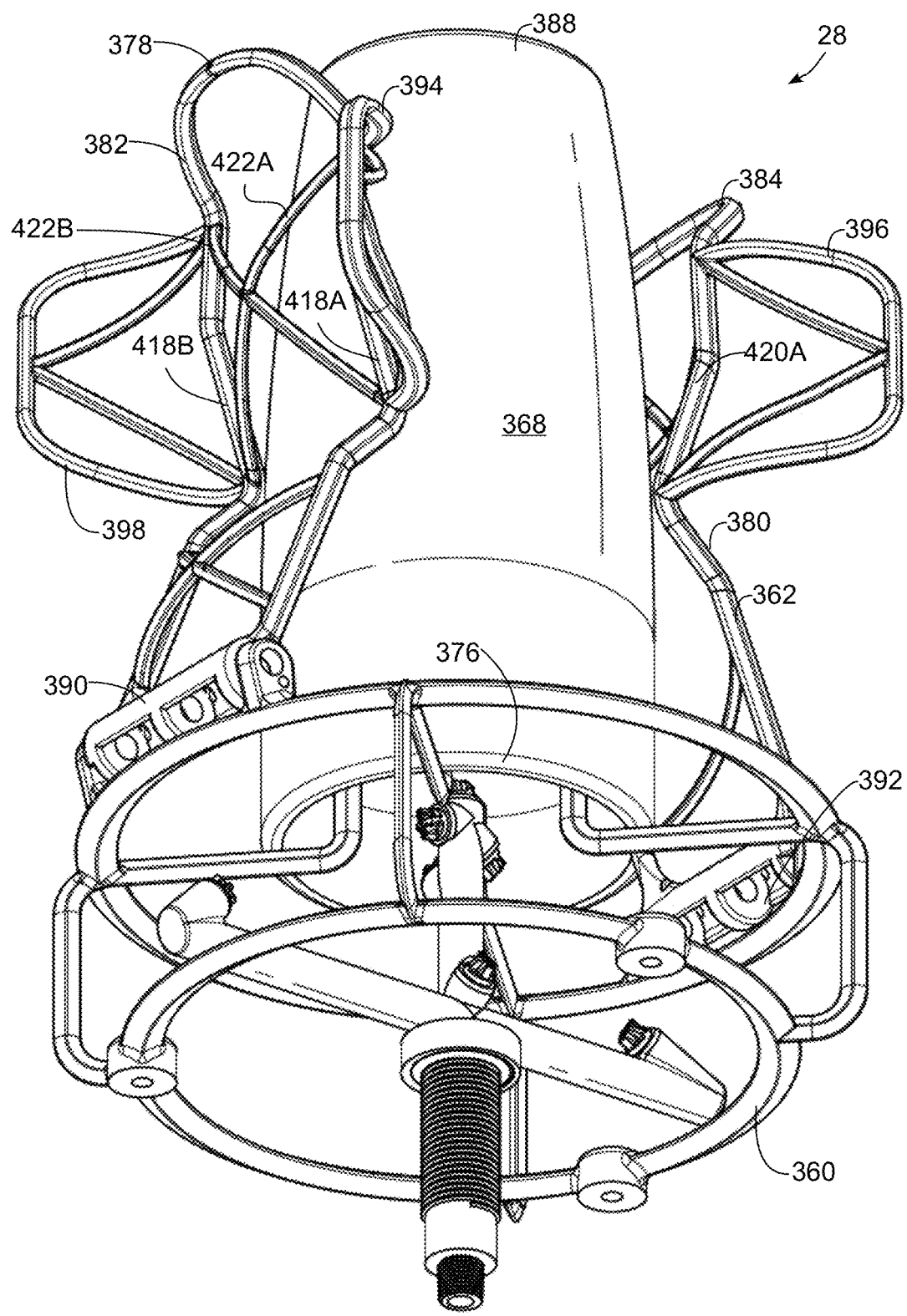
FIG. 16 is a lower perspective view of the holder and sprayer of FIG. 13.

With additional reference to FIG. 16, each container engaging portion 382 in the illustrated embodiment may include a pair of generally vertical members 418A-B, 420A-B that are joined to one another by a pair of crossing diagonal members 422A-B, 424A-B, with the contact points 414A-D, 416A-D defined at the intersections of these various members 418A-B, 420A-B, 422A-B and 424A-B. Moreover, in the illustrated embodiment, members 418A-B, 420A-B, 422A-B and 424A-B are bowed away from a beverage container when the beverage container is held by the holder in the inverted orientation, thereby minimizing the amount of surface area of the beverage container that is blocked by the structure of each gripper.

FIGS. 17-23 illustrate a number of alternate holder designs that may be used in other embodiments. FIG. 17, for example, illustrates a different holder 420 that includes a base 422 configured to support a beverage container when the beverage container is held by the holder in the inverted orientation, and a retainer 424 configured to support a sidewall of the beverage container when the beverage container is held by the holder in the inverted orientation to restrict lateral movement of the beverage container during the washing operation. The retainer 424 includes a C-shaped retaining ring 426 that is vertically separated from base 422 and includes a first opening 428 having a first width W1, as well as a retaining ring support 430 supporting C-shaped retaining ring 426 on base 422 on a side opposite opening 428 and defining a second opening 432 that is intermediate first opening 428 and base 422 and that has a second width W2 that is greater than first width W1. C-shaped retaining ring 426 and retaining ring support 430 in some embodiments may be integrally formed into a single bent or formed wire that includes a pair of vertical portions 434, 436 that define vertical supports that support the C-shaped retaining ring 426 on base 422.

By providing a C-shaped retaining ring, additional lateral support may be provided for taller beverage containers, and moreover, given that shorter beverage containers may have less of a need for lateral support, providing a retaining ring support that has a larger effective opening width than the C-shaped retaining ring allows for wider, shorter beverage containers to be accommodated. FIG. 18, for example, illustrates a short, wide beverage container, here a mug 438, that is supported by holder 420, but that does not extend all of the way to the elevation of C-shaped retaining ring 426, while FIG. 19 illustrates a taller, narrow beverage container, here a bottle 440, that extends through C-shaped retaining ring 426 and is thus laterally supported by the C-shaped retaining ring.

Returning to FIG. 17, base 422 in the illustrated embodiment may be formed of plastic, although other materials, e.g., various metal or wire configurations, may be used in other embodiments. Base 422 includes a plurality of (e.g., three) lip supports 442 that together operate as a substantially horizontal portion of the base to support the lip of a wide mouth beverage container, e.g., mug 438 as illustrated in FIG. 18. Lip supports 442 additionally support a central stabilizer ring 444 that operates as a substantially vertical portion of the base to support the shoulder of a narrow mount beverage container, e.g., bottle 440 as illustrated in FIG. 19.

Additional potential holder designs are illustrated in FIGS. 20-23. FIG. 20, for example, illustrates a holder 450 including a base 452 having an inverted wedding cake design to capture various beverage containers of different mouth sizes. Base 452, in particular, has an inclined portion 454 that defines a plurality of concentric annular supports capable of centering a beverage container in the holder. Moreover, in some embodiments, the inclined portion 454 may include a plurality of discrete steps 456. Base 452 may be molded plastic in some embodiments, and may be formed of a wire frame in other embodiments.

FIG. 21 illustrates a holder 460 including a base 462 with a plurality of base members 464 and a retainer 466 with a plurality of retainer members 468 configured to support the sidewall of a beverage container when the beverage container is held by the holder in the inverted orientation. In this design, base members 464 and retainer members 468 are joined by mechanical linkages 470 (e.g., planar quadrilateral linkages) such that a weight of the beverage container when supported on the plurality of base members 464 urges the plurality of retainer members 468 toward the sidewall of the beverage container.

FIG. 22 illustrates a similar holder 480 including a base 482 with a plurality of base members 484 and a retainer 486 with a plurality of retainer members 488 defined on the ends of base members 484. Each base member 484 includes a pivot point 490, and depending upon the width of the lip of the beverage container relative to the pivot points 490, each base member 484 will either rotate outwardly or inwardly. For wider beverage containers, e.g., mug 492, the lip is positioned radially outwardly from pivot points 490, causing outward rotation of each base member 484, with retainer members 488 positioned away from the beverage container. For narrower beverage containers, however, the lip may be positioned radially inwardly from pivot points 490, causing inward rotation of each base member 484, such that the weight of the beverage container urges the retainer members 488 against the sidewall of the beverage container.

Figure 23:
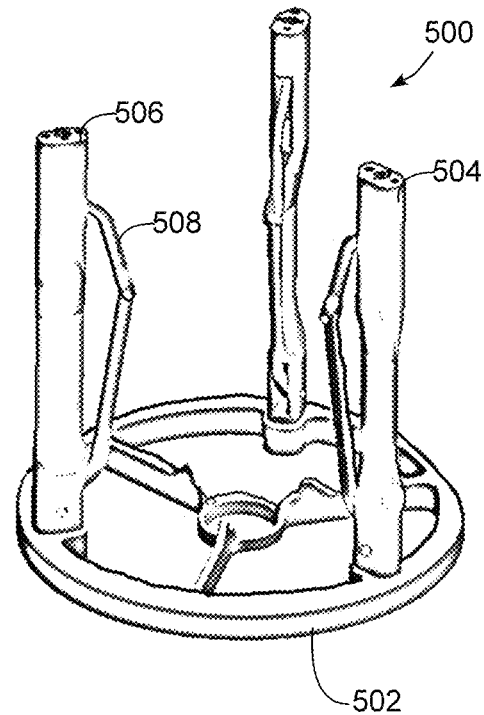

FIG. 23 illustrates a holder 500 including a base 502 similar to base 422 of holder 420 of FIG. 17, but with a retainer 504 formed by a set of vertical members 506 with spring-loaded supports 508 that are normally biased inwardly and configured to deflect radially outwardly when a beverage container is inserted downwardly into the holder.

Other holders may be used in other embodiments. Therefore, the invention is not limited to the particular holder designs illustrated herein.

Pop-Up Sprayer

Figure 24:
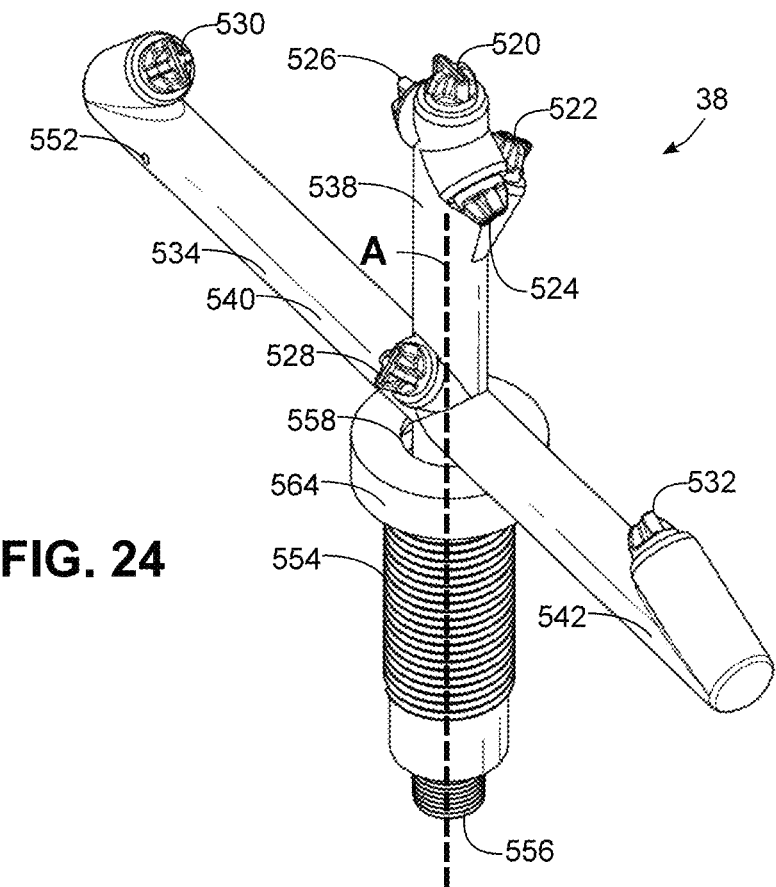
FIG. 24 is a perspective view of the sprayer of FIG. 13.

Now turning to FIG. 24, an example embodiment of sprayer 38 of spray assembly 30 is illustrated in greater detail. In the illustrated embodiment, sprayer 38 is a pop-up sprayer that is capable of rotating about an axis of rotation, which in the illustrated embodiment is coincident with axis of rotation A about which inner concentric housing member 62 rotates, as well as move between retracted and extended positions along the axis of rotation. Sprayer 38 includes a plurality of nozzles, e.g., seven nozzles 520, 522, 524, 526, 528, 530 and 532 in the illustrated embodiment, and as will become more apparent below, at least one of the nozzles (e.g., nozzle 520) is an interior nozzle oriented to spray wash fluid into an interior of a beverage container when the beverage container is held by the holder, and at least one of the nozzles (e.g., nozzle 530) is a lip nozzle oriented to spray wash fluid onto an outer lip of the beverage container when the beverage container is held by the holder.

Figure 25:
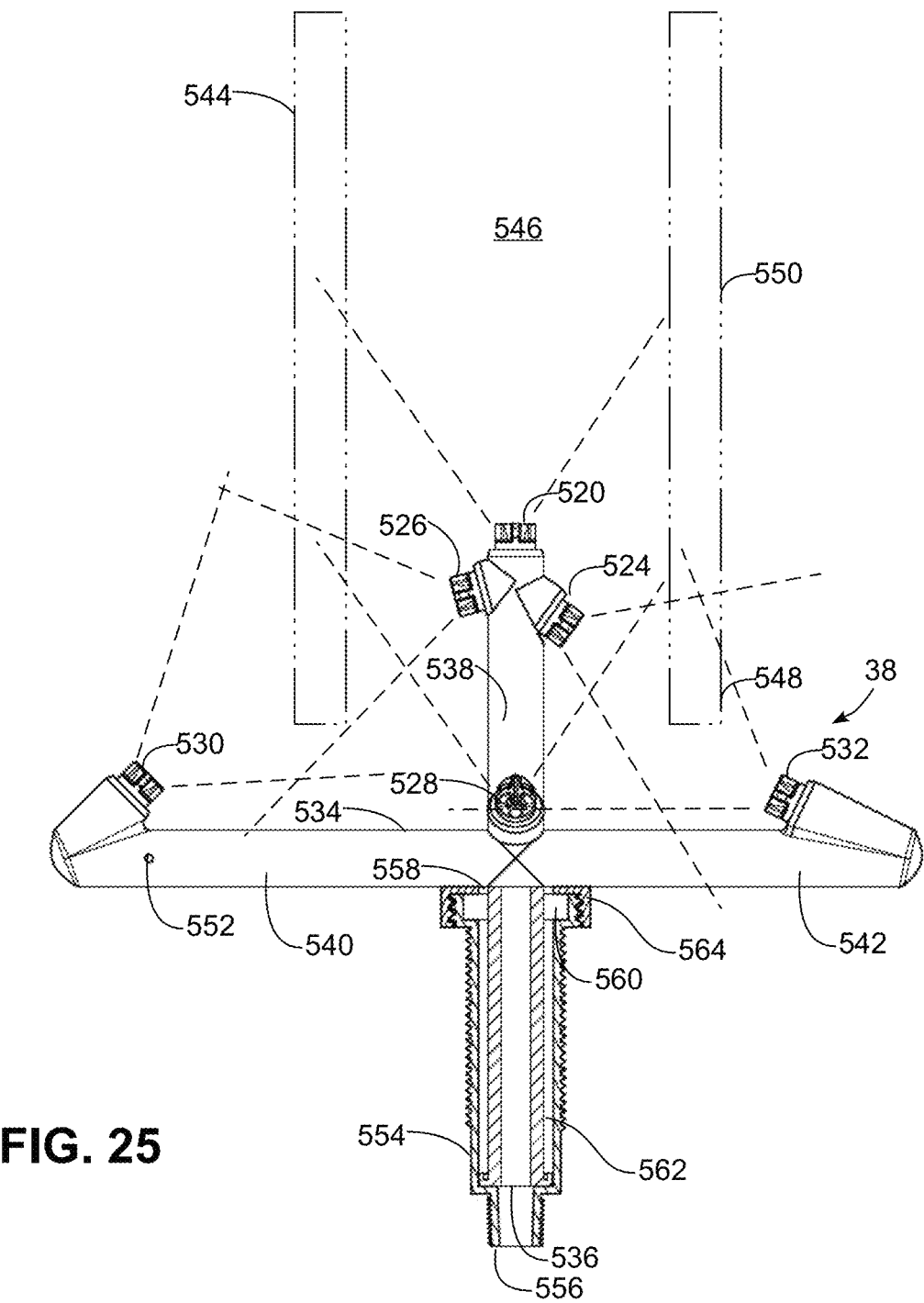
FIG. 25 is a side elevational view of the sprayer of FIG. 13, with a vertical cross section taken through the base thereof.

In the illustrated embodiment, and with additional reference to FIG. 25, nozzles 520-532 are supported by a manifold 534 including an inlet 536 configured to receive a pressurized wash fluid, an axial conduit 538 extending generally along the axis of rotation, and a pair of transverse conduits 540, 542 extending generally transverse to the axis of rotation, with each of conduits 538, 540, 542 in fluid communication with inlet 536.

Nozzles 520-528 are referred to herein as interior nozzles and are supported by, and in fluid communication with inlet 536 through, axial conduit 538, and at least a subset of these interior nozzles is axially offset from inlet 536 along the axis of rotation. While some of the wash fluid emitted by interior nozzles 520-528 may impact other regions of a beverage container (e.g., beverage container 544 of FIG. 25), interior nozzles 520-528 are primarily configured to spray wash fluid into the interior 546 of the beverage container, and as illustrated in FIG. 25, are generally arranged to provide overlapping spray patterns for different elevations within the interior of beverage container 544. The spray patterns may differ from one another along the axis of rotation, and the nozzles 520-528 may be axially and/or angularly offset from one another as shown in FIGS. 24 and 25.

In the illustrated embodiment, for example, interior nozzle 520 may be proximate a distal end of axial conduit 538 from inlet 536 and have a spray pattern with a center that is oriented along the axis of rotation. Interior nozzle 528 may be disposed proximate a junction between axial conduit 538 and transverse conduits 540, 542, and may have a spray pattern that is oriented to spray wash fluid onto the inner lip of the beverage container when the beverage container is held by the holder. Interior nozzles 522, 524 and 526 may also be positioned proximate the distal end of axial conduit 538, with interior nozzles 524 and 526 angularly offset from one another by about 180 degrees and having spray patterns oriented to spray wash fluid onto the inner lip of the beverage container when the beverage container is held by the holder, and interior nozzle 522 may have a spray pattern that is directed generally upwardly and overlaps the spray pattern of interior nozzle 520.

Nozzles 530, 532 are referred to herein as lip nozzles and are supported by, and in fluid communication with inlet 536 through, transverse conduits 540, 542, respectively. Each nozzle 530, 532 is radially offset from inlet 536 relative to the axis of rotation, and while some of the wash fluid emitted by lip nozzles 530, 532 may impact other regions of a beverage container, each lip nozzle 530, 532 is primarily configured to spray wash fluid at least partially onto an outer lip 548 of the beverage container 544, i.e., a portion of the beverage container lip or opening formed by an outer surface 550 of beverage container 544. As seen in FIG. 25, each lip nozzle 530, 532 may also focus spray onto other portions of the beverage container lip (e.g., an interior lip portion formed by an inner surface of the beverage container), and it will be appreciated that since it is generally the areas around the lip where a user's mouth may come into contact with the beverage container, lip nozzles 530, 532 in some embodiments may focus their efforts on spraying wash fluid at a sanitizing temperature to appropriately sanitize the areas of the beverage container that a user may likely come into contact with when drinking from the beverage container.

In the illustrated embodiment, transverse conduits 540, 542 are angularly offset from one another by about 180 degrees and both extend substantially normal to the axis of rotation. In other embodiments, different numbers of transverse conduits, e.g., as few as one or more than two, may be used, and the transverse conduits may extend at differing angles relative to the axis of rotation, so the invention is not limited to the particular configuration illustrated herein.

In addition, in the illustrated embodiment, sprayer 38 may additionally include one or more drive nozzles 552 that emit wash fluid in a tangential direction relative to the axis of rotation to drive rotation of sprayer 38 when spraying wash fluid. In other embodiments, the wash fluid sprayed by another nozzle 520-532 may impart sufficient torque to rotate the sprayer, and separate drive nozzles 552 may not be used. Further, in some embodiments an electric motor, pressurized air, or other electromechanical or mechanical drive system may be used to rotate the sprayer and/or move the sprayer between retracted and extended positions, whereby no separate drive nozzles 552 may be used.

Also in the illustrated embodiment, each nozzle 520-532 is a screw-in nozzle and is configured to threadably engage corresponding threaded apertures in manifold 534. As such, it may be desirable to form manifold 534 from a material capable of threadably engaging nozzles 520-532, e.g., metal. Each nozzle 520-532 also is configured with a fan spray pattern, e.g., with a spray width of about 15 to about 50 degrees in some embodiments. All nozzles 520-532 may be similarly configured in some embodiments, while in other embodiments, each nozzle 520-532 may include a different nozzle configuration tailored for its particular location and direction of spray. In the illustrated embodiment, the nozzles 520-532 are also clocked to a particular angle, e.g., such that the fan jets overlap and are all primarily oriented in the Y-plane. It will be appreciated that sprayer 38 may utilize different numbers, locations, types and configurations of nozzles in other embodiments, so the invention is not limited to the specific arrangement of nozzles illustrated herein. For example, in some embodiments, nozzles may be integrally molded into a manifold, and in some embodiments, different spray patterns, e.g., fluidic nozzles, jet nozzles, etc., may be used.

It will also be appreciated that, in the illustrated embodiment, sprayer 38 is predominantly limited to spraying wash fluid onto the interior of a beverage container as well as the inner and outer lip thereof (e.g., about 1 inch of the outer surface of the beverage container proximate the lip). While other regions of the outside of the beverage container may come into contact with wash fluid in some instances, the focus of sprayer 38 is on the areas of the beverage container that either come into contact with a beverage consumed by a user or come into contact with a user's mouth. Ultraviolet sanitizing assembly 32 instead focuses on the outer surface of a beverage container, including the outer lip; however, it is believed that limiting sprayer 38 to spraying the interior and outer lip of a beverage container with a wash fluid heated to a sanitizing temperature provides sufficient sanitization of a beverage container for many applications, and does so in a manner that reduces cycle time and water and energy consumption. In other embodiments, however, additional sprayers, e.g., located around the perimeter of the wash chamber, may be used to focus wash fluid onto the outside of a beverage container.

Figure 26:
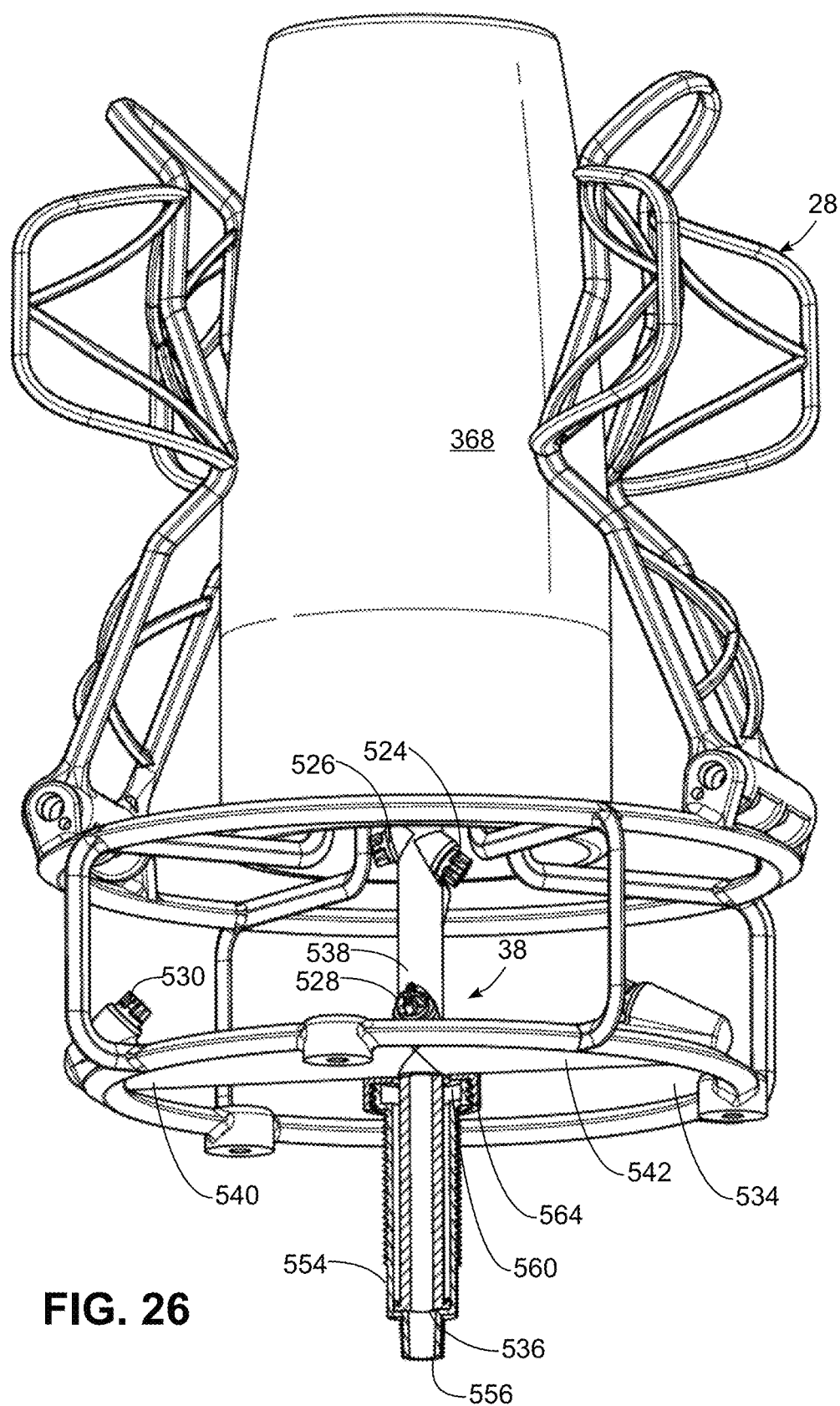
FIG. 26 is a side perspective view of the holder and sprayer of FIG. 13, with a vertical cross section taken through the base of the sprayer and the sprayer in a retracted position.
Figure 27:
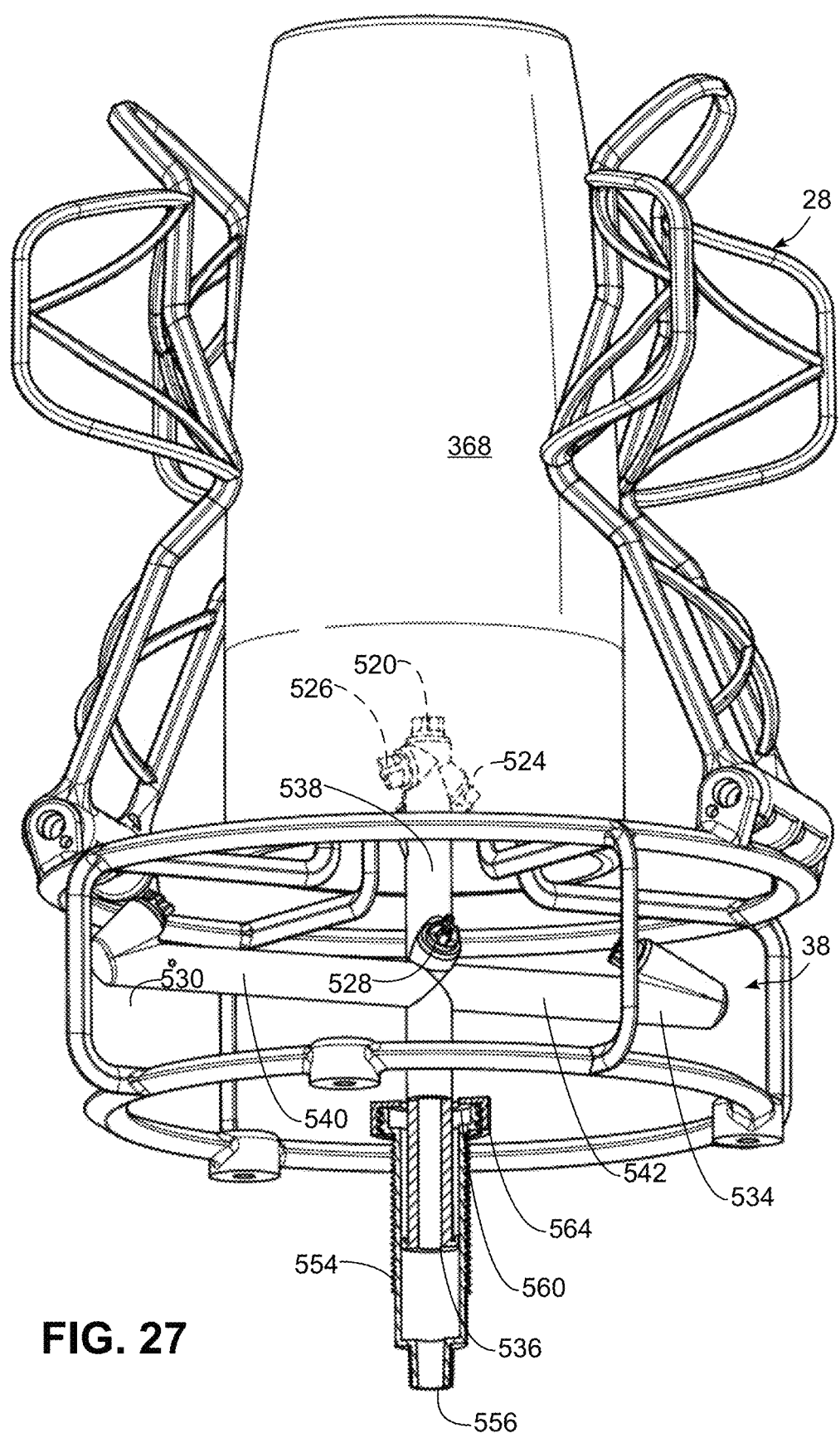
FIG. 27 is a side perspective view of the holder and sprayer of FIG. 13, with a vertical cross section taken through the base of the sprayer and the sprayer in an extended position.

With additional reference to FIGS. 26-27, manifold 534 is slidably received in a base 554. Base 554 includes an inlet 556 that receives pressurized wash fluid from pump 138, and an opening 558 that slidably and rotatably receives manifold 534. A seal 560 is disposed on base 554 to seal opening 558, while still allowing for slidable and rotary movement of manifold 534. A bias mechanism 562, e.g., a spring, is used to bias manifold 534, and thus sprayer 38, to a retracted position, e.g., as illustrated in FIGS. 24-26. However, manifold 534 is configured to overcome bias mechanism 562 and slide within base 554 to an extended position, e.g., as illustrated in FIG. 27, as a result of the pressure generated by wash fluid received through inlet 556 of base 554.

As illustrated in FIG. 26, when sprayer 38 is in the retracted position, axial conduit 538 of manifold 534 is generally at an elevation where the likelihood of contact between beverage container 368 and sprayer 38 during insertion or removal of the beverage container into or from holder 28 is minimized. However, as illustrated in FIG. 27, when sprayer 38 extends to the extended position due to the pressurization of manifold 534 when supplied with pressurized wash fluid by pump 138, axial conduit 538 of manifold 534 projects into the interior of beverage container 538 to position nozzles 520-526 within the interior, and nozzles 528-532 are positioned to focus spray onto the lip of the beverage container. When fluid flow to sprayer 38 from pump 138 is discontinued, the bias mechanism then urges the sprayer back to the retracted position.

Seal 560 in some embodiments may be a seal collar with living hinge, and a screw cap 564 may be used in some embodiments to secure manifold 534 within base 554. It will be appreciated that, given the high pressure utilized in some embodiments, other sealing arrangements may be used to minimize fluid and pressure loss through opening 558. In addition, while bias mechanism 562 is configured as a spring in the illustrated embodiment, other manners of biasing the sprayer to the retracted position may be used in other embodiments, e.g., a gravity bias mechanism that allows the manifold to drop to the retracted position based upon the weight of the manifold 534 and nozzles 520-532. Further, as noted above, in some embodiments an electric motor, solenoid, pressurized air, or other electromechanical or mechanical drive system may be used in some embodiments to transition sprayer 38 between the extended and retracted positions. Therefore, the invention is not limited to the particular sprayer design illustrated herein.

Beverage Container Washing System with Multiple Openings

Figure 28:
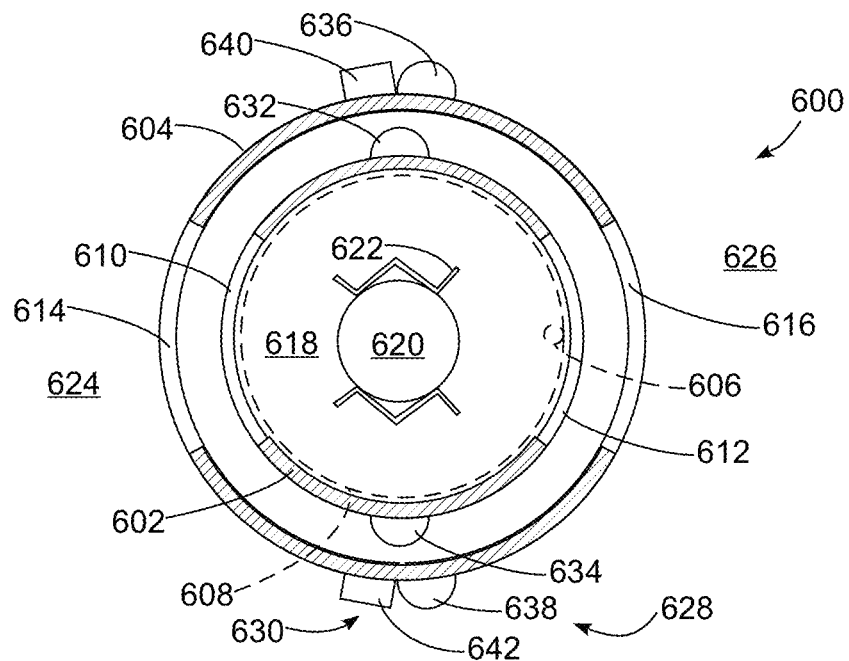
FIGS. 28 and 29 are functional top plan views of another beverage container washing system consistent with some embodiments of the invention.
Figure 29:
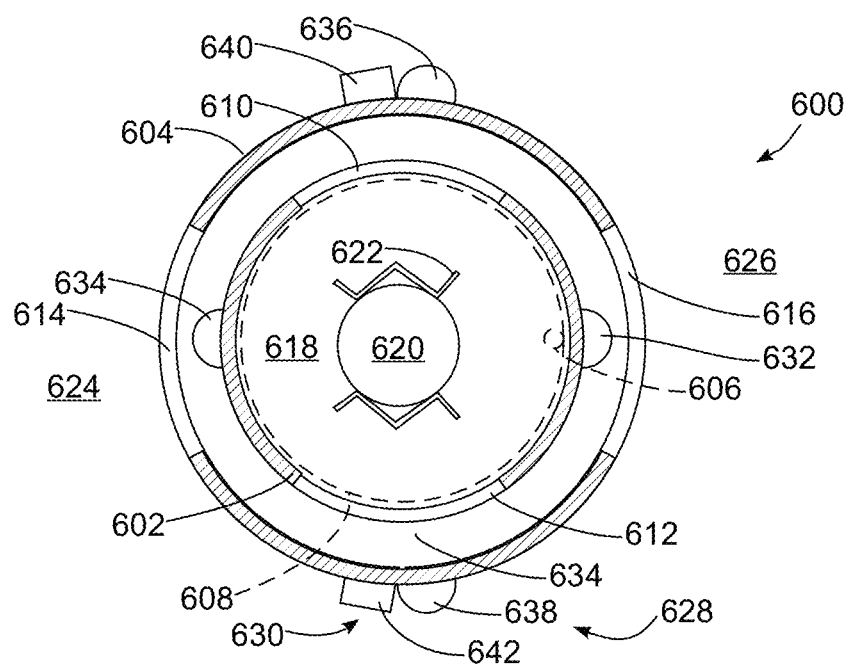

With reference to FIGS. 28 and 29, another beverage container washing system 600 consistent with the invention includes concentric housing members 602 and outer concentric housing member 604 configured as concentric domes that are generally dome shaped and have generally cylindrical sidewalls, with inner concentric housing member 602 is rotatable and driven by a drive motor (not shown) coupled to a gear 606 that drives a ring gear 608 attached to inner concentric housing member 602. Outer concentric housing member 604 is fixed or stationary. In this embodiment, inner concentric housing member 602 includes multiple openings, e.g., first and second openings 610, 612, while outer concentric housing member 604 includes first and second openings 614, 616 (e.g., entrance and exit openings, respectively), with each pair of openings disposed on substantially opposite sides from one another (e.g., about 180 degrees angularly offset from one another).

When inner concentric housing member 602 is rotated to the orientation illustrated in FIG. 28, it will be appreciated that openings 610 and 614 are aligned, as are openings 616. By doing so, access to a wash chamber 618 is provided, enabling for insertion and/or removal of a beverage container 610 into and/or out of a holder 622 through either aligned openings 610, 614 on side 624 of beverage container washing system 600 or aligned openings 612, 616 on side 626 of washing system 600. A rotation of inner concentric housing member 604 of about a quarter turn (about 90 degrees) in either direction results in the configuration illustrated in FIG. 29, where it may be seen that openings 610, 612 of inner concentric housing member 602 are now facing the sidewall of outer concentric housing member 604, and are unaligned with openings 614, 616. By doing so, wash chamber 618 is effectively closed off for a washing operation, and the sidewall of inner concentric housing member 602 minimizes the escape of wash fluid through openings 614, 616.

In this configuration, the orientation illustrated in FIG. 28 may be considered to function both as a loading position and an unloading position, with the orientation illustrated in FIG. 29 functioning as a washing position. Furthermore, it will be appreciated that an orientation where inner concentric housing member 602 is rotated 180 degrees relative to that illustrated in FIG. 28, where openings 610, 612 of inner concentric housing member 602 are aligned with openings 616, 614 of outer concentric housing member 604, respectively, may also be considered to represent loading and/or unloading positions. In addition, an orientation where inner concentric housing member 602 is rotated 180 degrees relative to that illustrated in FIG. 29 may also be considered to be a washing position. Moreover, transitioning between loading, washing and unloading positions may occur in different manners in different embodiments. In one embodiment, for example, a 90 degree rotation in one direction may transition from a loading position to a washing position, followed by another 90 degree rotation in the same direction to transition from the washing position to the unloading position. In another embodiment, a 90 degree rotation in one direction may transition from a loading position to a washing position, followed by a 90 degree rotation in the opposite direction to transition from the washing position to the unloading position. Further, it will be appreciated that with the use of two openings in the inner concentric housing member, no transition may be required between the unloading and loading positions at the completion of a washing operation, since the same relative positions may be used for both unloading and loading (although in other embodiments, a 180 degree rotation may be used if desired to transition between unloading and loading positions). Thus, while reference is made herein to separate loading and unloading positions, it will be appreciated that such positions may be represented by the same relative positions between the inner and outer concentric housing members 602, 604 in some embodiments.

Beverage container washing system 600 also illustrates an alternative ultraviolet sanitizing assembly 628 and dryer assembly 630 that may be suitable for use in some embodiments. Ultraviolet sanitizing assembly 628 in this embodiment includes a first pair of ultraviolet lights 632, 634 that are mounted to inner concentric housing member 602 in a similar manner to ultraviolet lights 40 as described above, with each positioned on opposite sides intermediate openings 610, 612, as well as a second pair of ultraviolet lights 636, 638 that are mounted to outer concentric housing member 604 and positioned on opposite sides intermediate openings 614, 616. In this configuration, and as seen in FIG. 29, when in a washing position, ultraviolet lights 632, 634, 636 and 638 are relatively evenly spaced about the periphery of wash chamber 618, thus providing substantially 360 degree exposure to the outside of beverage container 620. Moreover, ultraviolet lights 636 and 638 are respectively aligned with openings 610, 612 of inner concentric housing member 602 such that the sidewall of inner concentric housing member 602 does not block the ultraviolet radiation emitted by ultraviolet lights 636, 638.

Dryer assembly 630 in this embodiment includes a pair of stationary air knives 640, 642 that are supplied by a blower and, as illustrated in FIG. 29, are aligned with openings 610, 612 of inner concentric housing member 602 such that the sidewall of inner concentric housing member 602 does not block airflow from the air knives 640, 642. It will be appreciated that in some embodiments, air knives 640, 642 may be used instead of the top-down configuration illustrated in FIGS. 11-12, while in other embodiments, air knives 640, 642 may be used in addition to the aforementioned top-down configuration of FIGS. 11-12.

Other modifications may be made to the illustrated embodiments without departing from the spirit and scope of the invention. Therefore, the invention lies in the claims hereinafter appended.

What is claimed is:

1. An apparatus for washing a beverage container, comprising:
    a stationary base;
    inner and outer concentric housing members supported on the stationary base, the inner concentric housing member being disposed inwardly from the outer concentric housing member and forming at least a portion of a wash chamber with the stationary base, each of the inner and outer concentric housing members including an opening;
    a holder disposed within the wash chamber and configured to hold the beverage container during a washing operation; and
    a drive assembly coupled to the inner concentric housing member and configured to rotate the inner concentric housing member about an axis of rotation between first and second relative positions, wherein when in the first relative position, the respective openings of the inner and outer concentric housing members are aligned to permit external access to the holder in the wash chamber and when in the second relative position, the respective openings of the inner and outer concentric housing members are unaligned to restrict external access to the holder in the wash chamber during the washing operation;
    wherein the holder is positioned to hold the beverage container substantially along the axis of rotation during the washing operation, wherein the drive assembly includes an electric motor and a first gear, and wherein the inner concentric housing member includes a second gear circumscribing a perimeter of the inner concentric housing member and engaging the first gear.

2. The apparatus of claim 1, wherein each of the inner and outer concentric housing members fully circumscribe the axis of rotation.

3. The apparatus of claim 1, wherein when in the first relative position, the respective openings of the inner and outer concentric housing members permit external access to the holder in the wash chamber from a first location, wherein one of the inner and outer concentric housing members includes a second opening, and wherein the drive assembly is further configured to rotate the inner concentric housing member to a third relative position that provides external access to the holder in the wash chamber through the second opening and from a second location that is different from the first location.

4. The apparatus of claim 3, wherein the first and second locations are on opposite sides of the apparatus such that the beverage container may be placed within the wash chamber from the first location and removed from the wash chamber from the second location.

5. The apparatus of claim 1, wherein the drive assembly is configured to rotate the inner concentric housing member by rotating only the inner concentric housing member while the outer concentric housing member remains stationary.

6. The apparatus of claim 1, wherein the inner concentric housing member comprises an inner concentric dome and the outer concentric housing member comprises an outer concentric dome.

7. The apparatus of claim 6, wherein the opening of the outer concentric dome is an entrance opening, wherein the outer concentric dome includes an exit opening disposed on an opposite side of the outer concentric dome from the entrance opening, and wherein the drive assembly is configured to rotate the inner concentric dome to the first relative position prior to the washing operation to align the opening of the inner concentric dome with the entrance opening to permit insertion of the beverage container into the holder in the wash chamber, to rotate the inner concentric dome to the second relative position proximate a start of the washing operation to inhibit wash fluid sprayed during the washing operation from exiting through the entrance and exit openings of the outer concentric dome, and to rotate the inner concentric dome to a third relative position proximate an end of the washing operation to align the opening of the inner concentric dome with the exit opening to permit removal of the beverage container from the holder in the wash chamber.

8. The apparatus of claim 6, wherein the opening of the outer concentric dome is an entrance opening, wherein the outer concentric dome includes an exit opening disposed on an opposite side of the outer concentric dome from the entrance opening, wherein the opening in the inner concentric dome is a first opening and the inner concentric dome includes a second opening disposed on an opposite side of the inner concentric dome from the first opening, and wherein the drive assembly is configured to rotate the inner concentric dome to the first relative position prior to the washing operation to align one of the first and second openings of the inner concentric dome with the entrance opening to permit insertion of the beverage container into the holder in the wash chamber, to rotate the inner concentric dome to the second relative position proximate a start of the washing operation to inhibit wash fluid sprayed during the washing operation from exiting through the entrance and exit openings of the outer concentric dome, and to rotate the inner concentric dome to a third relative position proximate an end of the washing operation to align one of the first and second openings of the inner concentric dome with the exit opening to permit removal of the beverage container from the holder in the wash chamber.

9. The apparatus of claim 6, wherein the holder is disposed in a fixed location within the wash chamber and the stationary base includes a fixed collector configured to collect the wash fluid sprayed during the washing operation.

10. The apparatus of claim 9, further comprising a spray assembly including at least one sprayer disposed within the wash chamber and configured to spray the wash fluid onto the beverage container while the beverage container is held by the holder, wherein the at least one sprayer is supported by the stationary base.

11. The apparatus of claim 6, further comprising an ultraviolet sanitizing assembly including at least one ultraviolet light disposed within the wash chamber and configured to emit ultraviolet light toward the beverage container while the beverage container is held by the holder.

12. The apparatus of claim 11, wherein the at least one ultraviolet light is supported by and rotatable with the inner concentric dome.

13. The apparatus of claim 11, wherein the at least one ultraviolet light is stationary and supported by the outer concentric dome.

14. The apparatus of claim 6, further comprising a dryer assembly including at least one air outlet disposed in the inner concentric dome and configured to blow air onto the beverage container while the beverage container is held by the holder.

15. The apparatus of claim 1, further comprising:
a position detector configured to detect one or more relative positions between the inner and outer concentric housing members about the axis of rotation; and
a controller coupled to the drive assembly and the position detector and configured to control the drive assembly to rotate the at least one of the inner and outer concentric housing members between the first and second relative positions based at least in part on an output of the position detector.

16. An apparatus for washing a beverage container, comprising:
a base;
inner and outer concentric housing members supported on the base, the inner concentric housing member being disposed inwardly from the outer concentric housing member and forming at least a portion of a wash chamber, each of the inner and outer concentric housing members including an opening;
a holder disposed within the wash chamber and configured to hold the beverage container during a washing operation; and
a drive assembly coupled to the inner concentric housing member and configured to rotate the inner concentric housing member about an axis of rotation between first and second relative positions, wherein when in the first relative position, the respective openings of the inner and outer concentric housing members are aligned to permit external access to the holder in the wash chamber and when in the second relative position, the respective openings of the inner and outer concentric housing members are unaligned to restrict external access to the holder in the wash chamber during the washing operation;
wherein the holder is positioned to hold the beverage container substantially along the axis of rotation during the washing operation, and wherein the apparatus further includes an ultraviolet sanitizing assembly including a plurality of ultraviolet lights disposed within the wash chamber and configured to emit ultraviolet light toward the beverage container while the beverage container is held by the holder, the plurality of ultraviolet lights supported by and rotatable with the inner concentric housing member, the plurality of ultraviolet lights further spaced about the axis of rotation to emit ultraviolet light towards multiple sides of the beverage container during the washing operation;
wherein the ultraviolet sanitizing assembly further includes a stationary ultraviolet light supported by the outer concentric housing member and positioned to emit ultraviolet light towards the beverage container through the opening of the inner concentric housing member when the drive assembly rotates the inner concentric housing member to the second relative position.

* * * * *